United States Patent
Watarai et al.

(10) Patent No.: US 8,945,922 B2
(45) Date of Patent: Feb. 3, 2015

(54) GENERATING A MATURE NKT CELL FROM A REPROGRAMMED SOMATIC CELL WITH A T-CELL ANTIGEN RECEPTOR α-CHAIN REGION REARRANGED TO UNIFORM VA-JA IN A NKT-CELL SPECIFIC WAY

(75) Inventors: Hiroshi Watarai, Kanagawa (JP); Haruhiko Koseki, Kanagawa (JP); Masaru Taniguchi, Kanagawa (JP); Shin-ichiro Fujii, Kanagawa (JP)

(73) Assignee: Riken, Wako (JP)

( * ) Notice: Subject to any disclaimer, the term of this patent is extended or adjusted under 35 U.S.C. 154(b) by 496 days.

(21) Appl. No.: 13/062,453

(22) PCT Filed: Sep. 8, 2009

(86) PCT No.: PCT/JP2009/065695
§ 371 (c)(1),
(2), (4) Date: May 20, 2011

(87) PCT Pub. No.: WO2010/027094
PCT Pub. Date: Mar. 11, 2010

(65) Prior Publication Data
US 2011/0236362 A1  Sep. 29, 2011

(30) Foreign Application Priority Data

Sep. 8, 2008 (JP) .................. 2008-230292

(51) Int. Cl.
*C12N 5/02* (2006.01)
*A61K 31/7036* (2006.01)
*C12N 5/0783* (2010.01)
*C12N 5/074* (2010.01)
*A61K 35/12* (2006.01)

(52) U.S. Cl.
CPC ............ *A61K 31/7036* (2013.01); *A61K 35/12* (2013.01); *C12N 5/0646* (2013.01); *C12N 5/0696* (2013.01); *C12N 2501/23* (2013.01); *C12N 2501/2302* (2013.01); *C12N 2501/2307* (2013.01); *C12N 2501/2315* (2013.01); *C12N 2501/26* (2013.01); *C12N 2501/42* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2506/11* (2013.01); *C12N 2506/45* (2013.01)
USPC ............ 435/377; 435/373; 435/384; 435/386

(58) Field of Classification Search
CPC .............. C12N 2501/602; C12N 2501/603; C12N 2501/604; C12N 5/0646; C12N 5/0696; C12N 15/86; C12N 2501/605; C12N 2501/606; C12N 2501/2307; C12N 2501/2315; C12N 2501/39; C12N 2501/60; C12N 2501/608; C12N 2501/23; C12N 2501/2302; C12N 2501/26; C12N 2501/42; C12N 2506/11

See application file for complete search history.

(56) References Cited

U.S. PATENT DOCUMENTS

| | | |
|---|---|---|
| 2009/0047263 A1 | 2/2009 | Yamanaka et al. |
| 2009/0068742 A1 | 3/2009 | Yamanaka et al. |

FOREIGN PATENT DOCUMENTS

| | | |
|---|---|---|
| EP | 1 792 537 A1 | 6/2007 |
| EP | 1 997 884 A1 | 12/2008 |
| EP | 2 083 076 A1 | 7/2009 |
| WO | WO 2006/018998 A1 | 2/2006 |
| WO | WO 2007/069666 A1 | 6/2007 |
| WO | WO 2007/105797 A1 | 9/2007 |
| WO | WO 2008/038579 A1 | 4/2008 |

OTHER PUBLICATIONS

Inoue et al. Generation of Cloned Mice by Direct Nuclear Transfer from Natural Killer T Cells Current Biology, 2005, vol. 15, pp. 1114-1118.*
Stadtfeld et al. Induced pluripotent stem cells generated without viral integration. Science, vol. 322. pp. 945-949.*
Gonzales et al. Generation of mouse-induced pluripotent stem cells by transient expression of a single nonviral polycistronic vector. PNAS, 2009, vol. 106, pp. 8918-8922.*
Watari et al. Murine induced pluripotent stem cells can be derived from and differentiate into natural killer T cells. J. Clinical Invest., 2010, vol. 120, pp. 2610-2618.*

(Continued)

*Primary Examiner* — Deborah Crouch
(74) *Attorney, Agent, or Firm* — Leydig, Voit & Mayer, Ltd.

(57) ABSTRACT

Provided are an iPS cell derived from a somatic cell such as an NKT cell, having the α-chain region of the T cell antigen receptor gene rearranged to uniform Vα-Jα in an NKT cell receptor-specific way, NKT cells differentiated from the iPS cell, a method of creating the same, and an immune cell therapy agent prepared using cells differentiated from the iPS cell. Also provided are an iPS cell having TCRα rearranged to NKT-TCR (NKT-iPS cell), obtained by contacting a somatic cell, such as an NKT cell, having the α-chain region of the T cell antigen receptor gene rearranged to uniform Vα-Jα in an NKT cell receptor-specific way, with nuclear reprogramming factors, isolated NKT cells obtained by differentiating the iPS cell ex vivo (iPS-NKT cell), a method of generating CD4/CD8-double positive NKT cells (DP-NKT cells) and mature NKT cells from NKT-iPS cells by altering the combination of feeder cells and/or cytokines, a method of expanding the iPS-NKT cells, and an NKT cell cytotherapy agent comprising NKT cells activated with α-galactosyl ceramide (α-GalCer), or iPS-NKT cells, and α-GalCer in combination.

17 Claims, 33 Drawing Sheets

(56) References Cited

OTHER PUBLICATIONS

Williams et al. Differentiation of NK1.11, Ly491 NK Cells from flt31Multipotent Marrow Progenitor Cells1 J. Immunology, 1999, vol. 163, pp. 2648-2656.*
Strelchenko et al. Embryonic Stem Cells from Morula, Methods in Enzymology, 2006, vol. 418, pp. 93-108.*
Stojkovlc et al. Derivation, growth and applications of human embryonic stem cells. Reproduction, 2004, vol. 128, pp. 259-267.*
Yamanaka et al. Strategies and new developments in the generation of patient-specific pluripotent stem cells. Cell Stem Cell, 2007, vol. 1, pp. 39-49.*
Okita et al. Generation of mouse induced pluripotent stem cells without viral vectors. Science. vol. 322, pp. 949-953, 2009.*
Ohno et al. Runx proteins are involved in regulation of CD122, Ly49 family and IFN-g expression during NK cell differentiation International Immunology, 2007, vol. 20, pp. 71-79.*
Aoi et al., *Science*, 321: 699-702 (2008).
Eminli et al., *Stem Cells*, 26: 2467-2474 (2008).
Hanna et al., *Cell*, 133: 250-264 (2008).
Hanna et al., *Cell*, 134: 365 (2008).
Inoue et al., *Current Biology*, 15: 1114-1118 (2005).
Jiang et al., *European Journal of Immunology*, 35: 1193-1200 (2005).
Kim et al, Nature, 454: 646-650 (2008).
Lowry et al., *Proc. Natl. Acad. Sci. USA*, 105(8): 2883-2888 (2008).
Nakagawa et al., *Nature Biotechnology*, 26(1): 101-106 (2008).
Okita et al., *Nature*, 448: 313-317 (2007).
Park et al., *Nature*, 451: 141-146 (2008).
Shimizu et al., *Journal of Immunology*, 177: 3484-3492 (2006).
Stadtfeld et al., *Current Biology*, 18: 890-894 (2008).
Shi et al., *Cell Stem Cell*, 2: 525-528 (2008).
Takahashi et al., *Cell*, 126: 663-676 (2006).
Takahashi et al., *Cell*, 131: 861-872 (2007).
Wakao et al, *FASEB, J.*, 22: 2223-2231 (2008).
Wernig et al., *Nature Biotechnology*, 26(8): 916-924 (2008).
Yu et al., *Science*, 318: 1917-1920 (2007).
Schmitt et al., *Nature Immunology*, 5(4): 410-417 (2004).
Graf et al., *Immunity*, 28(5): 606-608 (2008).

\* cited by examiner

FIG. 11
(A)
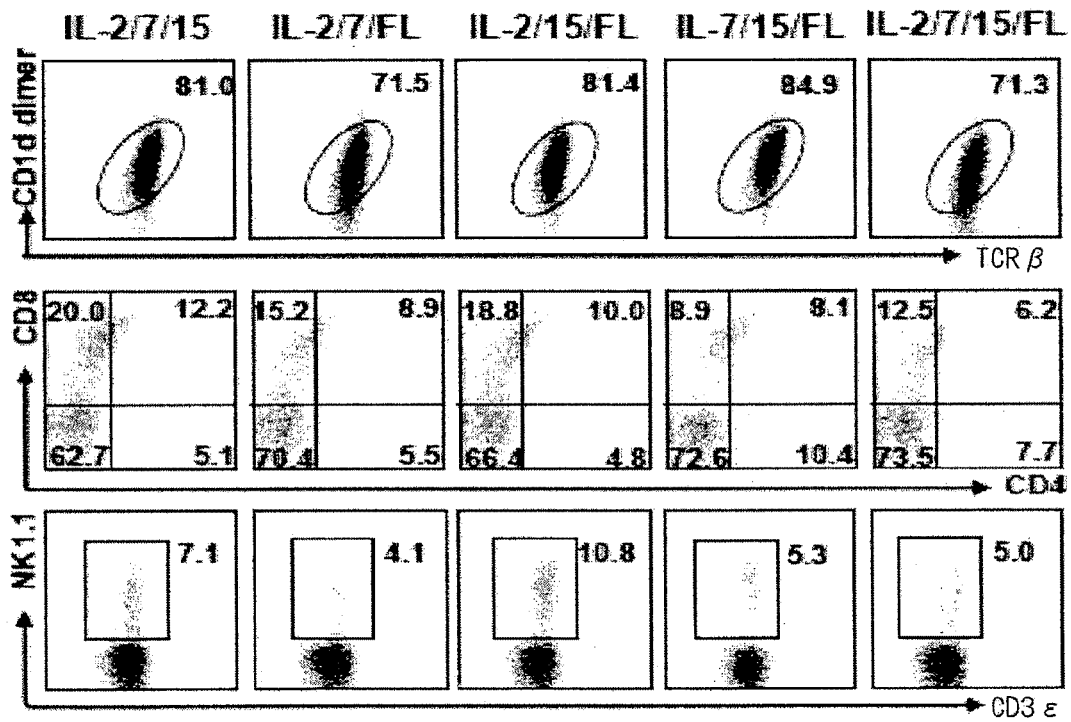
(B)
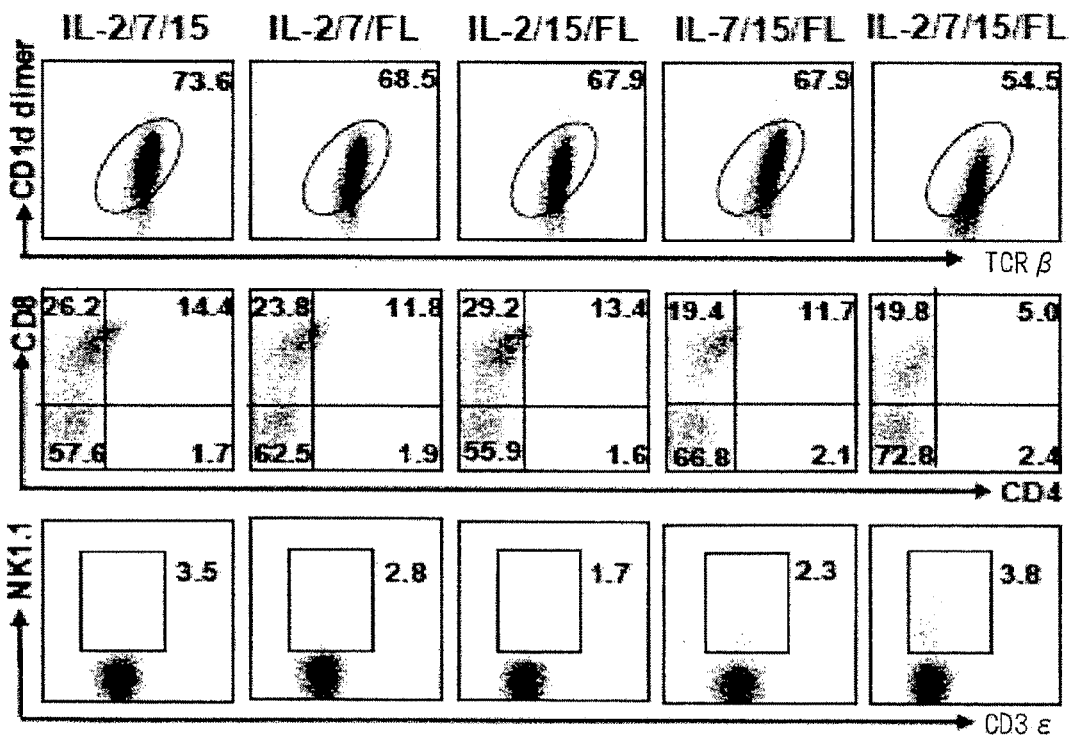

FIG. 16

```
            Vα14 ||
Vα  ...gtggggatagaggttcagccttaggagggctgcattttggagctgcatgttgtcatacctgacatc... | Cα
              V  G  D  R  G  S  A  L  G  R  L  H  F  G  A  G  T  Q  L  I  V  I  P  D  I
                                            Jα18

Vβ8.1  | Dβ1 |       Jβ1.2                          | Cβ1
Vβ  ...agcagtgagccagcaaaactccgactacacctttcggctcaggaccaggcttttggtaatagaggatctg...
        S  S  E  P  A  N  S  D  Y  T  F  G  S  G  T  R  L  L  V  I  E  D  L
```

FIG. 24
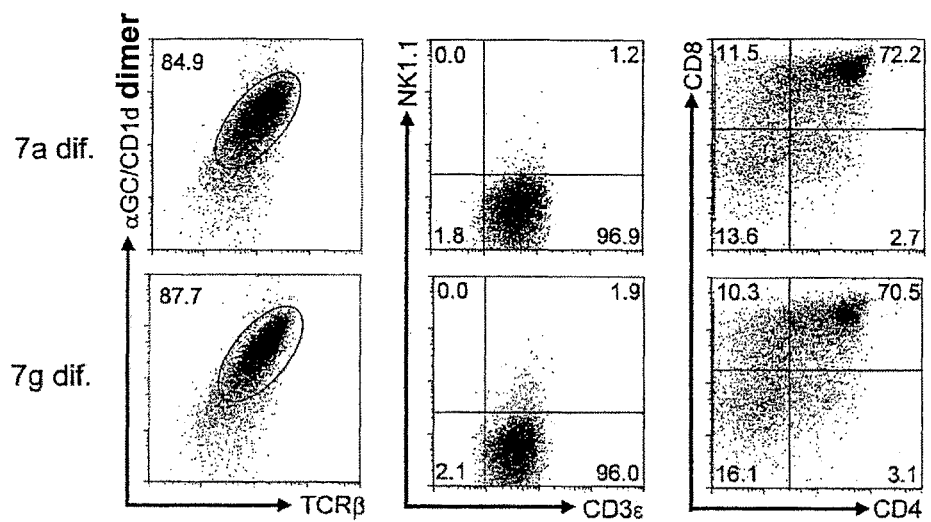
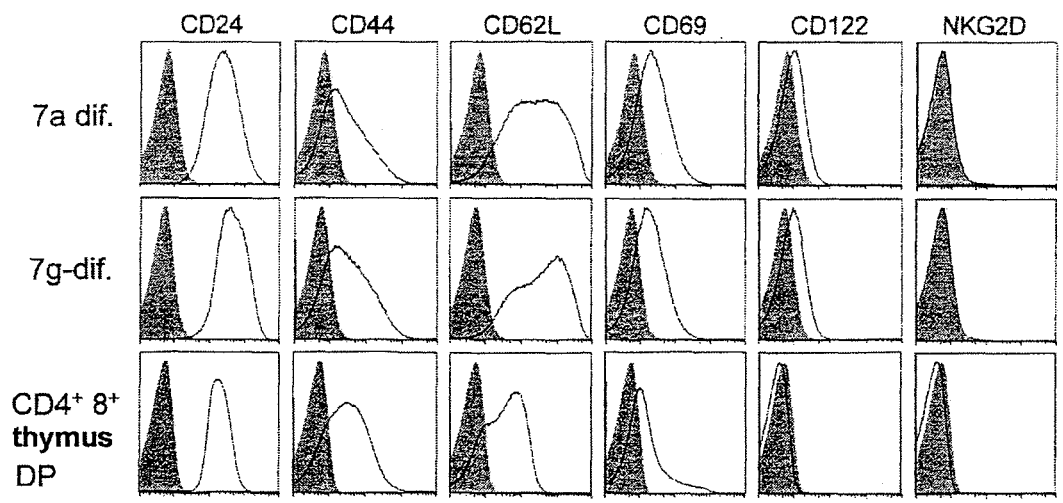

FIG. 29
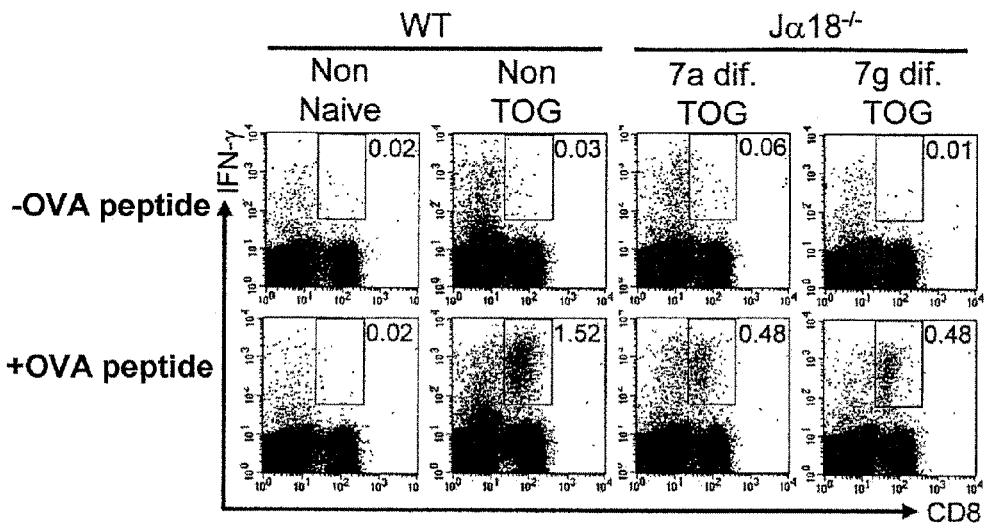
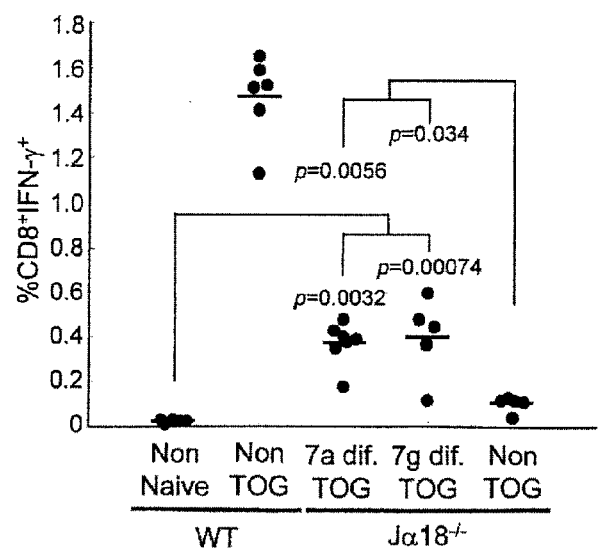

FIG. 33
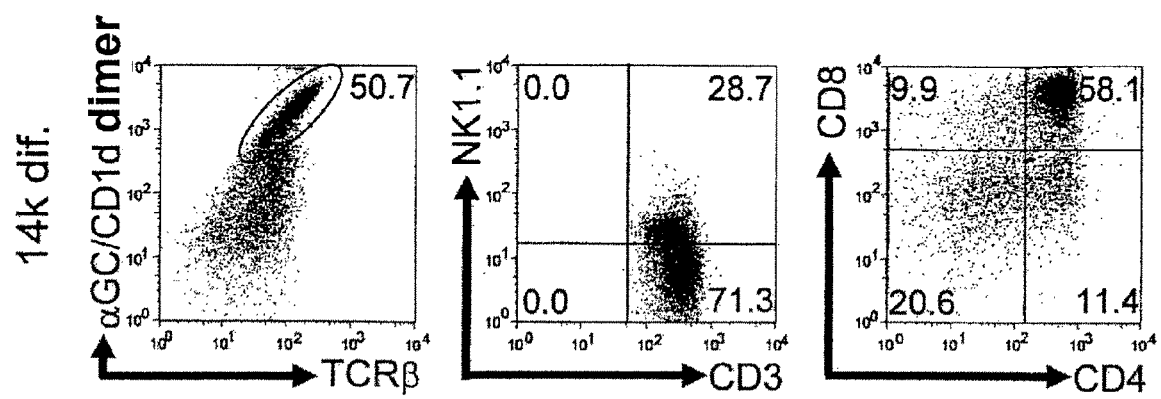
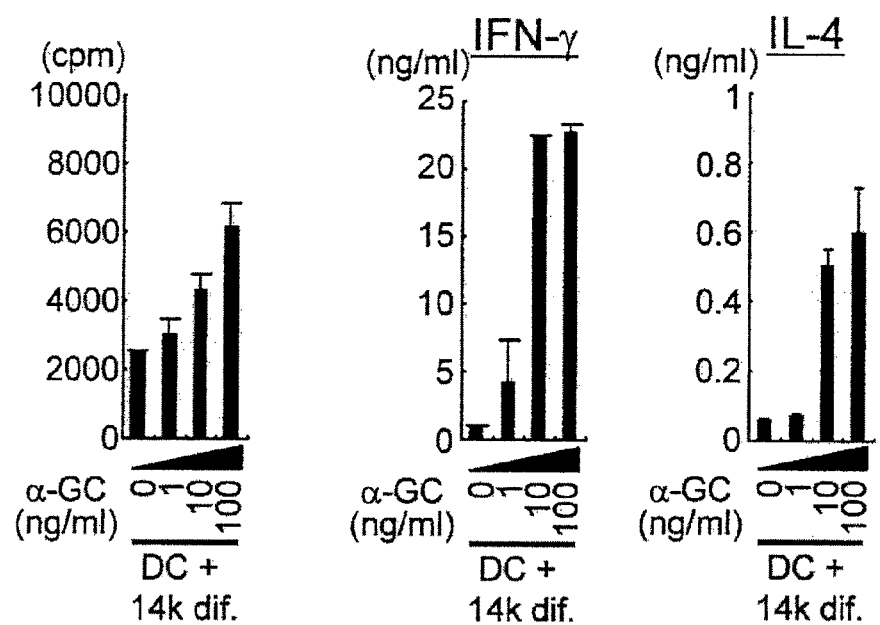

GENERATING A MATURE NKT CELL FROM A REPROGRAMMED SOMATIC CELL WITH A T-CELL ANTIGEN RECEPTOR α-CHAIN REGION REARRANGED TO UNIFORM Vα-Jα IN A NKT-CELL SPECIFIC WAY

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,281 bytes ASCII (Text) file named "707814SequenceListing.txt," created May 20, 2011.

TECHNICAL FIELD

The present invention relates to an NKT cell-derived induced pluripotent stem (hereinafter referred to as iPS) cell, NKT cells derived from the IFS cell, a method of producing the same, and a use application thereof. The present invention also relates to an iPS cell derived from a somatic cell wherein the α-chain region of the T cell antigen receptor gene is rearranged to uniform Vα-Jα in an NKT cell receptor-specific way, NKT cells derived from the iPS cell, a method of producing the same, and a use application thereof.

BACKGROUND ART iPS cells possess capabilities of differentiation and tissue formation equivalent to those of embryonic stem cells (ES cells). Because of inducibility from human primary culture cells, iPS cells are cells potentially possessing the capability of playing a central role in regenerative medicine. Yamanaka et al. established an iPS cell that possesses pluripotency as do ES cells by transferring four factors (Oct3/4, Sox2, Klf4, c-Myc) to mouse embryonic fibroblasts (MEF) (Non-patent Document 1). In addition to MEF, they succeeded in establishing mouse iPS cells from other various cells (Non-patent Documents 2 and 3), organs (Non-patent Document 4) and the like. Furthermore, in humans as well, establishment of iPS cells from human somatic cells using the same technique was reported (Non-patent Documents 5-8).

An aspect that can be a major barrier to ensuring the efficacy and safety of iPS cells in the context of their clinical application resides in the diversity thereof. It is speculated that the functioning of iPS cells differs among different lines depending on the individual's genetic background, the type of cells, the degree of reprogramming, the stage of genesis at which the cells are immortalized, and the like. In fact, even in mouse ES cells, the gene expression pattern differs widely depending on the genetic background, and the differentiation competence varies widely among different lines. It has already been found by Yamanaka et al. that in human iPS cells as well, the gene expression pattern differs widely among different lines (Non-patent Document 5). Therefore, it is anticipated that the differentiation competence and tumorigenesis tendency vary considerably among different iPS cells.

Also, there is a room for further improvement in the nuclear reprogramming protocol; various improved protocols have been reported (Non-patent Documents 9-14).

The hematopoietic-immune system has long been positioned as a subject of regenerative medicine or cytotherapy, from blood transfusion to bone marrow transplantation and cord blood transplantation, and these therapies have been shown to be substantially effective. It has also been shown that in mice and humans, a variety of hematopoietic-immune system cells can be differentiation-induced from ES cells. This shows that induction of hematopoietic-immune system cells from iPS cells would be potentially effective as a therapy within the conventional framework.

Natural killer T (NKT) cells, which is in a series of lymphocytes that constitute the immune system, play a central role in antitumor immunity and defensive reactions to infectious diseases by the adjuvant effect of the Th1 cytokine IFN-γ; the lack of NKT cells leads to infectious death. Meanwhile, because immune responses are controlled by IL-10, which is a Th2 cytokine produced by NKT cells, the cells are also responsible for control of transplantation immune reaction and suppression of the onset of autoimmune diseases. As stated above, NKT cells occupy the central part in immune control; therefore, α-galactosyl ceramide (α-GalCer), which is a glycolipid ligand of NKT cells that allows artificial control of the cellular function thereof, is not the only currently available immune response regulator; in fact, NKT cells are already in some clinical applications in lung cancer patients, and the results of phase II clinical studies that have been conducted to date show that the mean survival time is extended as much as 4-5 times compared with chemotherapy.

However, in cancer patients who are subjects of NKT cell immunotherapy, NKT cell count reductions and functional defects are seen (see, for example, Non-patent Document 15), so that there are some cases in which activation of NKT cells sufficient to obtain a therapeutic effect cannot be accomplished merely by administration of α-GalCer-pulsed dendritic cells. In this case, it is possible that NKT cells are collected from the patient or another person of the same HLA type and expanded, and then returned (transplanted) to the patient; however, NKT cells are usually present in extremely small amounts at not more than 0.1% of peripheral blood lymphocytes, and it is uneasy to mass-expand them. Therefore, provided that an NKT cell clone can be expanded in large amounts by reprogramming the NKT cells collected, and then allowing them to differentiate and mature again, it is expected that the therapeutic effect of NKT cell immunotherapy can be improved.

However, finally differentiated cells are less easy to reprogram, compared with undifferentiated cells; no reports of induction of iPS cells from T cells or NKT cells have been presented to date. For B cells, it was reported that iPS cells cannot be induced with what are called the four factors or three factors (Oct3/4, Sox2, Klf4) only, their induction often requiring the use of another gene as a nuclear reprogramming factor (Non-patent Document 3). However, increasing the number of transgenes is feared to intensity safety concerns, including the potential tumorigenesis of the cells differentiated from iPS cells. Furthermore, even if iPS cell were established from an NKT cell, it would remain unknown whether differentiation from the iPS cell to functional mature NKT cells could be induced.

PRIOR ART REFERENCES

Non-Patent Documents non-patent document 1: Cell. 2006 Aug. 25; 126(4): 663-676.
non-patent document 2: Nature. 2007 Jul. 19; 448(7151): 313-317. Epub2007 Jun. 6.
non-patent document 3: Cell. 2008 Apr. 18; 133(2): 250-264. Erratum in: Cell. 2008 Jul. 25; 134(2): 365.
non-patent document 4: Science. 2008 Aug. 1; 321(5889): 699-702. Epub2008 Feb. 14.
non-patent document 5: Cell. 2007 Nov. 30; 131(5): 861-872.

non-patent document 6: Science. 2007 Dec. 21; 318(5858): 1917-1920. Epub 2007 Nov. 20.
non-patent document 7: Nature. 2008 Jan. 10; 451(7175): 141-146. Epub 2007 Dec. 23.
non-patent document 8: Proc Natl Acad Sci USA. 2008 Feb. 26; 105(8): 2883-2888. Epub 2008 Feb. 15.
non-patent document 9: Nat. Biotechnol. 2008 January; 26(1): 101-106. Epub 2007 Nov. 30.
non-patent document 10: Nat. Biotechnol. 2008 August; 26(8): 916-924. Epub 2008 Jul. 1.
non-patent document 11: Utikal J S, Arnold K, Jaenisch R, Hochedlinger K. Reprogramming of neural progenitor cells into iPS cells in the absence of exogenous Sox2 expression. Stem Cells. Epub 2008 Jul. 17.
non-patent document 12: Nature. 2008 Jul. 31; 454(7204): 646-650. Epub 2008 Jun. 29.
non-patent document 13: Cell Stem Cell. 2008 Jun. 5; 2(6): 525-528.
non-patent document 14: Curr Biol. 2008 Jun. 24; 18(12): 890-894. Epub 2008 May 22.
non-patent document 15: J. Immunol. 2006 177: 3484-3492

SUMMARY OF THE INVENTION

Problems to be Solved by the Invention

It is an object of the present invention to provide an NKT cell-derived iPS cell, NKT cells differentiated from the iPS cell, and methods of creating the same. It is another object of the present invention to provide an iPS cell derived from a somatic cell having the α-chain region of the T cell antigen receptor gene rearranged to uniform Vα-Jα in an NKT cell receptor-specific way, NKT cells differentiated from the iPS cell, and methods of creating the same. It is still another object of the present invention to provide an immune cell therapy agent and the like prepared using cells differentiated from the iPS cell.

Means of Solving the Problems

The present inventors conducted extensive investigations to solve the above-described problems, and unexpectedly succeeded in establishing a cell having the α-chain region of the T cell antigen receptor (TCR) gene rearranged to Vα14-Jα18, and possessing properties characteristic of iPS cells, such as proliferation competence, pluripotency, and an ES cell-like gene expression pattern (hereinafter referred to as "NKT-iPS cell"), by introducing only the four factors Oct3/4, Sox2, Klf4, and c-Myc into a mouse spleen-derived NKT cell using a retrovirus. The present inventors also succeeded in establishing an NKT-iPS cell by introducing the aforementioned four factors into an embryonic fibroblast from an NKT cell clone mouse obtained by transferring the nucleus of a mouse spleen-derived NKT cell into an enucleated oocyte. Furthermore, the present inventors tested various combinations of feeder cells and cytokines, and as a result, succeeded in mass-expanding mature NKT cells from the NKT-iPS cell obtained, confirmed that the NKT cell is functional in vivo, and have developed the present invention.

Accordingly, the present invention relates to the following:
[1] A cloned cell, obtained by contacting nuclear reprogramming factors with a somatic cell having the α-chain region of the T cell antigen receptor gene rearranged to uniform Vα-Jα in an NKT cell receptor-specific way, wherein the cloned cell has the α-chain region of the T cell antigen receptor gene rearranged to uniform Vα-Jα in an NKT cell receptor-specific way, and possesses pluripotency and replication competence.
[2] The cell described in [1] above, wherein the somatic cell is an NKT cell.
[3] The cell described in [1] above, wherein the somatic cell is a fibroblast.
[4] The cell described in any one of [1] to [3] above, wherein the nuclear reprogramming factors are Oct3/4, Sox2, Klf4 and c-Myc or nucleic acids that encode the same, or Oct3/4, Sox2 and Klf4 or nucleic acids that encode the same.
[5] The cell described in any one of [1] to [4] above, wherein the somatic cell is of human derivation.
[6] An isolated NKT cell, obtained by differentiating the cell described in any one of [1] to [5] above ex vivo.
[7] The cell described in [6] above, wherein the cell is NK1.1-positive.
[8] The cell described in [6] above, wherein Th1-dominant cytokine production is induced by contact with an α-galactosyl ceramide-presenting dendritic cell.
[9] A method of generating a CD4/CD8-double positive NKT cell, comprising co-culturing the cell described in any one of [1] to [5] above with a stromal cell that expresses a Notch ligand.
[10] A method of expanding NKT cells, comprising co-culturing a CD4/CD8-double positive NKT cell obtained by the method described in [9] above with a stromal cell in the presence of three or more cytokines selected from the group consisting of interleukin-2, interleukin-7, interleukin-15 and Flt3 ligands.
[11] The method described in [10] above, wherein the cytokines include interleukin-2, interleukin-15 and an Flt3 ligand.
[12] A method of generating an NK1.1-positive NKT cell, comprising co-culturing a CD4/CD8-double positive NKT cell obtained by the method described in [9] above with a stromal cell that does not express a Notch ligand.
[13] The method described in [12] above, wherein the cultivation is performed in the presence of interleukin-15.
[14] A method of generating an activated NKT cell, comprising contacting an NKT cell obtained by the method described in any one of [9] to [13] above with an α-galactosyl ceramide-presenting dendritic cell.
[15] An NKT cell cytotherapy agent, comprising an activated NKT cell obtained by the method described in [14] above.
[16] An NKT cell cytotherapy agent, comprising the cell described in any one of [6] to [8] above or a cell obtained by the method described in any one of [9] to [14] above, and α-galactosyl ceramide in combination.
[17] A method of producing a cloned cell having the α-chain region of the T cell antigen receptor gene rearranged to uniform Vα-Jα in an NKT cell receptor-specific way, and possessing pluripotency and replication competence, comprising contacting nuclear reprogramming factors with a somatic cell having the α-chain region of the T cell antigen receptor gene rearranged to uniform Vα-Jα in an NKT cell receptor-specific way.
[18] The method of production described in [17] above, wherein the somatic cell is an NKT cell.
[19] The method of production described in [18] above, wherein the NKT cell contacted with the nuclear reprogramming factors has been stimulated with an anti-CD3 antibody and an anti-CD28 antibody in the presence of IL-2 and IL-12.
[20] The cell described in [17] above, wherein the somatic cell is a fibroblast.
[21] The method of production described in any one of [17] to [20] above, wherein the nuclear reprogramming factors are Oct3/4, Sox2, Klf4 and c-Myc or nucleic acids that encode the same, or Oct3/4, Sox2 and Klf4 or nucleic acids that encode the same.

[22] The method of production described in any one of [17] to [21] above, wherein the somatic cell is of human derivation.

Effect of the Invention

According to the present invention, it is possible to induce functionally mature NKT cells that are equivalent to peripheral NKT cells in terms of the expression of cell surface antigens, and that possess glycolipid ligand responsiveness, via iPS cells in vitro.

BRIEF DESCRIPTION OF THE DRAWINGS

FIG. 11 is a drawing showing the expression of invariant TCRα, the expression of CD4/CD8, and the expression of NK1.1 in cells obtained by co-culturing DP-NKT cells with stromal cells that (A) do not express/(B) express a Notch ligand using various combinations of cytokines.

FIG. 16 is a drawing showing the base sequence of the T cell receptor region of an NKT clone mouse with C57BL/6 background.

FIG. 24 is a drawing showing the expression of cell surface markers in cells differentiation-induced from NKT-iPS cell clones 7a and 7g in vitro.

FIG. 29 is a drawing showing the induction of antigen specific CD8-positive T cells by cells 7a dif. and 7g dif. differentiation-induced in vitro.

FIG. 33 is a drawing showing an in vitro functional evaluation of cells differentiation-induced from NKT-iPS clone 14k.

MODES FOR EMBODYING THE INVENTION

Figure 1:
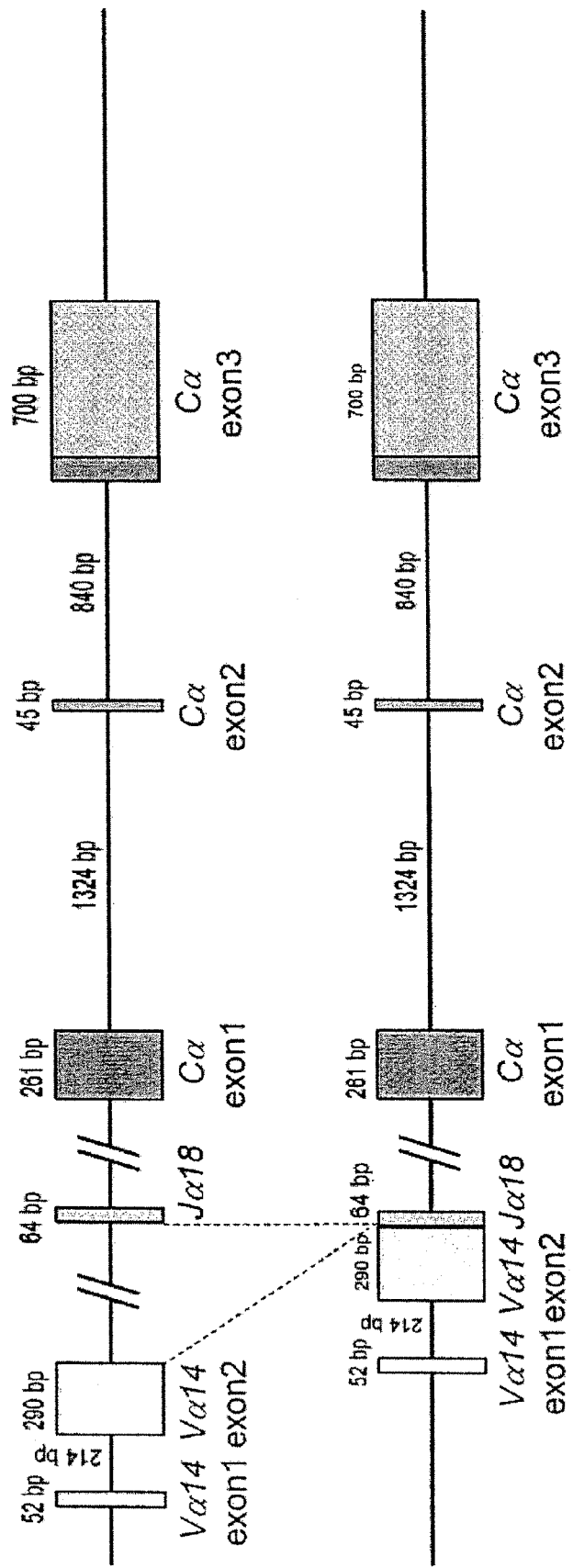
FIG. 1 is a schematic diagram of the TCRα gene loci of wild type and NKT cells.

The present invention provides a cell having the α chain region of the TCR gene (TCRα) rearranged to uniform Vα-Jα, and possessing properties characteristic of iPS cells, such as replication competence, pluripotency, and an ES cell-like gene expression pattern (NKT-iPS cell). As used herein, "an iPS cell" refers to a cell that has acquired pluripotency and replication competence conferred artificially by contacting nuclear reprogramming factors with a somatic cell, and that is similar to ES cells in terms of gene expression profile. Here, "pluripotency" means the ability to differentiate into a plurality of series of immunohepatopoietic cells such as NKT cells, T cells, B cells, erythrocytes, macrophages and progenitor cells thereof, as well as into one or more cell series other than the hematopoietic-immune system, and is distinguished from multipotency in hematopoietic stem cells and multipotent progenitor cells. "Replication competence" means the ability for a cell to continue to expand in a particular environment (for example, conditions suitable for culturing ES cells) while retaining the above-described "pluripotency". Furthermore, "similar to ES cells in terms of gene expression profile" means that the correlation coefficient r between the data set of gene expression in the subject cells and the data set of gene expression in ES cells is 0.9 or more. ES cells for the comparison include ES cells generated from a fertilized egg derived from the same species, preferably from the same strain, ES cells generated from an embryo transplanted with the nucleus of an NKT cell, and the like.

The NKT-iPS cell of the present invention can be a cell having the α chain region of the TCR gene (TCRα) rearranged to uniform Vα-Jα in an NKT cell receptor-specific way, and possessing properties characteristic of iPS cells, such as replication competence, pluripotency, and an ES cell-like gene expression pattern. The term "an NKT cell receptor-specific way" will be described below.

The NKT-iPS cell of the present invention can be established by contacting a somatic cell having the α chain region of the TCR gene (TCRα) rearranged to uniform Vα-Jα in an NKT cell receptor-specific way, such as NKT cells, with nuclear reprogramming factors. Herein, the "NKT cell" is not particularly limited, as far as either TCRα region is rearranged to uniform Vα-Jα, and it is used with a meaning encompassing not only mature NKT cells (characterized by, for example, NK1.1$^+$/CD3ε$^+$), but also progenitor cells thereof (cells characterized by, for example, CD4$^+$/CD8$^+$ and the like). NKT cells can be isolated from the spleen, lymph node, peripheral blood, cord blood and the like by a method known per se, for example, flow cytometry using an antibody against the above-described cell surface markers and a cell sorter. In the case of mice, it is preferable to collect NKT cells from the spleen or lymph node, wherein the abundance ratio of NKT cells is high; however, in the case of humans, it is desirable, from the viewpoint of low invasiveness and the ease of preparation, that the NKT cells be prepared from peripheral blood, cord blood and the like.

The NKT cell used in the present invention may be derived from any animal species that permits the establishment of NKT-iPS cells by contacting nuclear reprogramming factors with the NKT cell; specifically, those of human or mouse derivation can be mentioned, and human-derived NKT cells are preferred. The human or mouse that serves as the source of NKT cells collected is not particularly limited; however, when the NKT-iPS cells obtained are to be used for immune cell therapy in humans, it is particularly preferable, from the viewpoint of prevention of graft rejection, that the NKT cells be collected from the patient or from another person having the same HLA type as that of the patient. When the NKT-iPS cells obtained are not to be administered (transplanted) to a human, but used as, for example, a source of cells for screening for evaluating a patient's drug susceptibility or the presence or absence of adverse reactions, it is necessary to collect the NKT cells from the patient or from another person with the same genetic polymorphism correlating with the drug susceptibility or adverse reactions.

The NKT cells prepared from the spleen, lymph node, peripheral blood, cord blood and the like by the above-described method may be immediately contacted with nuclear reprogramming factors to induce NKT-iPS cells, or may also be preserved under freezing by a conventional method, thawed just before use, and cultured, and then contacted with nuclear reprogramming factors to induce NKT-iPS cells. Therefore, it is possible, for example, to preserve NKT cells prepared from the recipient's own spleen, lymph node, peripheral blood, cord blood and the like under freezing for a long time while he or she is healthy, to induce NKT-iPS cells from the NKT cells and auto-transplant cells, tissues and the like obtained by differentiation induction therefrom when cell transplantation becomes necessary in a later year.

NKT cells are presumably functionally uniform immunocompetent cells characterized by rearrangement of either TCRα region to uniform Vα-Jα (Vα24-Jα18 in humans, Vα14-Jα18 in mice). In the NKT-iPS cell of the present invention, rearrangement to NKT-TCR is conserved.

The NKT-iPS cell of the present invention can be established by contacting a somatic cell with nuclear reprogramming factors, even if the somatic cell is other than an NKT cell, as far as the somatic cell has the α-chain region of the T cell antigen receptor gene rearranged to uniform Vα-Jα in an NKT cell receptor-specific way. An NKT cell receptor is a T cell receptor that is expressed specifically in NKT cells, and that specifically recognizes a galactosyl ceramide (α-GalCer) presented onto CD1d. The α chain of an NKT cell receptor is normally rearranged to Vα24-Jα18 in humans, and to Vα14-Jα18 in mice. Therefore, rearrangement in an NKT cell receptor-specific way means gene rearrangement in the α chain region such that the V-J combination in the α-chain region of the T cell antigen receptor is Vα24-Jα18 in humans and Vα14-Jα18 in mice, and that the TCRα obtained is capable of constituting the NKT cell receptor. Such a somatic cell can be prepared by a method known per se. For example, such a somatic cell can be a somatic cell collected from an NKT cell clone animal prepared by transplanting the nucleus of an NKT cells to an enucleated cell (e.g., oocyte), and subjecting the cell to a specified operation. Generating a clone animal is described in, for example, WO2006/018998 and the like. The somatic cell can be, for example, a fibroblast and the like, and is preferably a fibroblast (particularly an embryonic fibroblast).

The somatic cell having the α-chain region of the T cell antigen receptor gene rearranged to uniform Vα-Jα in an NKT cell receptor-specific way can be a cell derived from an optionally chosen mammalian species. Examples of such mammalian species include primates such as humans and monkeys, mice, rats, hamsters, guinea pigs, and other rodents, rabbits, cats, dogs, horses, bovines, sheep, goat, and pigs. When the somatic cell is one established by nuclear transplantation, the somatic cell established by nuclear transplantation can also be a cell established by transplanting the nucleus of an NKT cell to an enucleated cell derived from the same mammalian species as the nucleus, or a cell established by transplanting the nucleus to an enucleated cell derived from a mammalian species different from the donor of the nucleus.

In the present invention, "a nuclear reprogramming factor" may be composed of any substance such as a proteinous factor(s) or a nucleic acid that encodes the same (including forms incorporated in a vector) or a low molecular compound, as far as it is a substance (a group of substances) capable of inducing cells possessing pluripotency and replication competence from a somatic cell such as an NKT cell. When the nuclear reprogramming factor is a proteinous factor or a nucleic acid that encodes the same, the following combinations, for example, are preferable (hereinafter, only the names for proteinous factors are shown).

(1) Oct3/4, Klf4, Sox2, c-Myc (Sox2 is replaceable with Sox1, Sox3, Sox15, Sox17 or Sox18; Klf4 is replaceable with Klf1, Klf2 or Klf5; c-Myc is replaceable with T58A (active mutant), N-Myc, or L-Myc)
(2) Oct3/4, Klf4, Sox2
(3) Oct3/4, Klf4, c-Myc
(4) Oct3/4, Sox2, Nanog, Lin28
(5) Oct3/4, Klf4, c-Myc, Sox2, Nanog, Lin28
(6) Oct3/4, Klf4, Sox2, bFGF
(7) Oct3/4, Klf4, Sox2, SCF
(8) Oct3/4, Klf4, c-Myc, Sox2, bFGF
(9) Oct3/4, Klf4, c-Myc, Sox2, SCF When bearing in mind the use of the NKT-iPS cells obtained for therapeutic purposes, the combination of the three factors Oct3/4, Sox2 and Klf4 is preferable out of these combinations. Meanwhile, when not bearing in mind the use of the NKT-iPS cells for therapeutic purposes (for example, use as a research tool for drug discovery screening and the like, and the like), the four factors Oct3/4, Klf4, Sox2 and c-Myc or the five factors consisting of the same four factors and Lin28 or Nanog are preferred. Particularly preferably, the nuclear reprogramming factors in the present invention are the four factors Oct3/4, Klf4, Sox2 and c-Myc.

In the present invention, NKT-iPS cells can be acquired only with the above-described nuclear reprogramming factors in common use for reprogramming fibroblasts and the like, thus obviating the use of other factors as reported in the case of B cells. This makes it possible to reduce the potential tumorigenesis in the cells and tissues differentiation-induced from an NKT-iPS cell.

Information on the mouse and human cDNA sequences of the aforementioned proteinous factors is available with reference to the NCBI accession numbers mentioned in WO 2007/069666 (in the publication, Nanog is described as ECAT4; mouse and human cDNA sequence information on Lin28 can be acquired by referring to the following NCBI accession numbers NM_145833 and NM_024674, respectively). Those skilled in the art are easily able to isolate these cDNAs. A proteinous factor for use as a nuclear reprogramming factor can be prepared by inserting the cDNA obtained into an appropriate expression vector, transferring the vector into a host cell, culturing the cell, and recovering the recombinant proteinous factor from the culture obtained. Meanwhile, when the nuclear reprogramming factor used is a nucleic acid that encodes a proteinous factor, the cDNA obtained is inserted into a viral or plasmid vector to construct an expression vector, and the vector is subjected to the step of nuclear reprogramming.

Contact of a nuclear reprogramming factor with a somatic cell such as an NKT cell can be achieved using a method known per se for protein transfer into cells when the substance is a proteinous factor. Such methods include, for example, the method using a protein transfer reagent, the method using a protein transfer domain (PTD) fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), and the like. The transfer can be achieved per the protocols attached to these reagents, a common procedure being as described below. A nuclear reprogramming factor is diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as *drosophila*-derived AntP, HIV-derived TAT, and HSV-derived VP22. A fusion protein expression vector incorporating a cDNA of a nuclear reprogramming factor and a PTD sequence is prepared to allow the recombinant expression of the fusion protein, and the fusion protein is recovered for use in for transfer. This transfer can be achieved as described above, except that no protein transfer reagent is added.

Microinjection, a method of placing a protein solution in a glass needle having a tip diameter of about 1 μm, and injecting the solution into a cell, ensures the transfer of the protein into the cell.

However, taking into account the ease of transfer into a somatic cell such as an NKT cell, a nuclear reprogramming factor is used preferably in the form of a nucleic acid that encodes a proteinous factor, rather than the factor as it is. The nucleic acid may be a DNA or an RNA, or a DNA/RNA chimera, and may be double-stranded or single-stranded. Preferably, the nucleic acid is a double-stranded DNA, particularly a cDNA.

A cDNA of a nuclear reprogramming factor is inserted into an appropriate expression vector comprising a promoter capable of functioning in a host somatic cell such as an NKT cell. Useful expression vectors include, for example, viral vectors such as retrovirus, lentivirus, adenovirus, adeno-associated virus and herpesvirus, plasmids for the expression in animal cells (e.g., pA1-11, pXT1, pRc/CMV, pRc/RSV, pcDNAI/Neo) and the like.

A kind of vector used can be chosen as appropriate according to the intended use of the NKT-iPS cells obtained. For example, adenovirus vector, plasmid vector, adeno-associated virus vector, retrovirus vector, lentivirus vector and the like can be used.

Examples of promoters used in expression vectors include the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the MoMuLV LTR, the CMV promoter, the SRα promoter and the like.

The expression vector may contain as desired, in addition to a promoter, an enhancer, a polyA addition signal, a selection marker gene, a SV40 replication origin and the like. Examples of useful selection marker genes include the dihydrofolate reductase gene and the neomycin resistance gene.

An expression vector harboring a nucleic acid as a nuclear reprogramming factor can be transferred into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. Meanwhile, a plasmid vector can be transferred into a cell using the lipofection method, liposome method, electroporation method, calcium phosphate co-precipitation method, DEAE dextran method, microinjection method, gene gun method and the like.

When the nuclear reprogramming factor is a low-molecular compound, contact of the substance with somatic cells such as NKT cells can be achieved by dissolving the substance at an appropriate concentration in an aqueous or non-aqueous solvent, adding the substance solution to a medium suitable for cultivation of somatic cells such as NKT cells isolated from a human or mouse (for example, a minimal essential medium (MEM), Dulbecco's modified Eagle medium (DMEM), RPMI1640 medium, 199 medium, and F12 medium containing cytokines such as IL-2, IL-7, SCF, and Flt3 ligands, and about 5 to 20% fetal bovine serum, and the like) so that the nuclear reprogramming factor concentration will fall in a range that is sufficient to cause nuclear reprogramming in somatic cells such as NKT cells and does not cause cytotoxicity, and culturing the cells for a given period. The nuclear reprogramming factor concentration varies depending on the kind of nuclear reprogramming factor used, and is chosen as appropriate over the range of about 0.1 nM to about 100 nM. Duration of contact is not particularly limited, as far as it is sufficient to achieve nuclear reprogramming of the cells; usually, the nuclear reprogramming factor may be allowed to be co-present in the medium until a positive colony emerges.

When generating the NKT-iPS cell of the present invention by contacting nuclear reprogramming factors with an NKT cell, the NKT cell to be contacted with the nuclear reprogramming factors may have been stimulated with an anti-CD3 antibody and an anti-CD28 antibody in the presence of IL-2 and IL-12. Stimulation of the NKT cell can be achieved by, for example, adding IL-2 and IL-12 to a medium suitable for culturing NKT cells as described above, and culturing the NKT cell on a culture dish with an anti-CD3 antibody and an anti-CD28 antibody bound to the surface thereof for a given time. The anti-CD3 antibody and the anti-CD28 antibody may be used in a mode dissolved in the medium, as far as they are able to stimulate the NKT cell. The concentration of each antibody as bound to the plate is 0.1-100 µg/ml; the concentration of each antibody as used in a mode dissolved in the medium is 0.1-100 µg/ml. The concentration of each of IL-2 and IL-12 added can be chosen as appropriate over the range of, for example, 0.1-100 ng/ml. The duration of cultivation is not particularly limited, as far as it is a sufficient time to ensure the proliferation of the NKT cell and stimulation with the anti-CD3 antibody and the anti-CD28 antibody; the duration is normally about 3 days to 1 month, for example, 1 week. The NKT cell stimulated through this step is contacted with the nuclear reprogramming factors.

As stated in an Example below, including this step makes it possible to establish NKT-iPS cells more efficiently.

In recent years, various substances that improve the efficiency of establishment of iPS cells, which has traditionally been low, have been proposed one after another. When brought into contact with somatic cell such as NKT cells together with the aforementioned nuclear reprogramming factors, these establishment efficiency improvers are expected to further raise the efficiency of establishment of NKT-iPS cells.

Examples of iPS cell establishment efficiency improvers include, but are not limited to, histone deacetylase (HDAC) inhibitors [for example, low-molecular inhibitors such as valproic acid (VPA) (Nat. Biotechnol., 26(7): 795-797 (2008)), trichostatin A, sodium butyrate, MC 1293, and M344; nucleic acid-based expression inhibiting agents such as siRNAs and shRNAs against HDAC (e.g., HDAC1 siRNA Smartpool$^o$ (registered trademark) (Millipore), HuSH 29mer shRNA Constructs against HDAC1 (OriGene) and the like); and the like], G9a histone methyltransferase inhibitors [e.g., low-molecular inhibitors such as BIX-01294 (Cell Stem Cell, 2: 525-528 (2008)); nucleic acid-based expression inhibitors such as siRNAs and shRNAs against G9a (for example, G9a siRNA (human) (Santa Cruz Biotechnology) and the like; and the like], and the like. The nucleic acid-based expression inhibitors may be in the form of expression vectors harboring a DNA that encodes an siRNA or shRNA.

Contact of an iPS cell establishment efficiency improver with somatic cells such as NKT cells can be achieved as described above for each of three cases: (a) the improver is a proteinous factor, (b) the improver is a nucleic acid that encodes the proteinous factor, and (c) the improver is a low-molecular compound.

An iPS cell establishment efficiency improver may be brought into contact with somatic cells such as NKT cells simultaneously with a nuclear reprogramming factor, or either one may be contacted in advance, as far as the efficiency of establishment of NKT-iPS cells from somatic cells such as NKT cells is significantly improved, compared with the absence of the improver. In an embodiment, for example, when the nuclear reprogramming substance is a nucleic acid that encodes a proteinous factor and the iPS cell establishment efficiency improver is a chemical inhibitor, the iPS cell establishment efficiency improver can be added to the medium after the cell is cultured for a given length of time after the gene transfer treatment, because the nuclear reprogramming substance involves a given length of time lag from the gene transfer treatment to the mass-expression of the proteinous factor, whereas the iPS cell establishment efficiency improver is capable of rapidly acting on the cell. In another embodiment, when a nuclear reprogramming factor and an iPS cell establishment efficiency improver are both used in the form of a viral vector or plasmid vector, for example, both may be simultaneously transferred into the cell.

The somatic cells such as NKT cells separated from a human or mouse can also be pre-cultured using a medium known per se that is suitable for their cultivation (for example, a minimal essential medium (MEM), Dulbecco's modified Eagle medium (DMEM), RPMI1640 medium, 199 medium, and F12 medium containing cytokines such as IL-2, IL-7, IL-15, SCF, and Flt3 ligands, and about 5 to about 20% fetal bovine serum, and the like).

When a transfection reagent such as a cationic liposome, for example, is used in contacting with nuclear reprogramming factors (and an iPS cell establishment efficiency improver), it is sometimes preferable that the medium be previously replaced with a serum-free medium to prevent a reduction in the transfer efficiency. After the nuclear reprogramming factors (and iPS cell establishment efficiency improver) are contacted, the cells can be cultured under conditions suitable for the cultivation of, for example, ES cells. In the case of human cells, it is preferable that the cultivation be carried out with the addition of basic fibroblast growth factor (bFGF) as a differentiation suppressor to an ordinary medium. Meanwhile, in the case of mouse cells, it is desirable that Leukemia Inhibitory Factor (LIF) be added in place of bFGF. Usually, the cells are cultured in the co-presence of fetal-mouse-derived fibroblasts (MEFs) treated with radiation or an antibiotic to terminate the cell division thereof, as feeder cells. Usually, STO cells and the like are commonly used as MEFs, but for inducing iPS cells, SNL cells [McMahon, A. P. & Bradley, A. Cell 62, 1073-1085 (1990)] and the like are commonly used.

A candidate colony of NKT-iPS cells can be selected by a method with drug resistance and reporter activity as indicators, and also by a method based on visual examination of morphology. As an example of the former, a colony positive for drug resistance and/or reporter activity is selected using a recombinant somatic cell such as a recombinant NKT cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Meanwhile, examples of the latter method based on visual examination of morphology include the method described by Takahashi et al. in Cell, 131, 861-872 (2007). Although the method using reporter cells is convenient and efficient, it is desirable, from the viewpoint of safety, that colonies be selected by visual examination when the NKT-iPS cells are prepared for the purpose of applying to human treatment; even by visual morphological examination, a candidate colony of NKT-iPS cells can be selected well efficiently.

Confirmation of the identity of the cells of the selected colony as NKT-iPS cells can be achieved by various testing methods known per se, for example, by measuring the expression of a group of genes including an ES cell-specific gene (for example, Oct3/4, Sox2, Nanog, Cripto, Dax1, ERas, Fgf4, Esg1, Rex1, Zfp296 and the like) using RT-PCR (see FIG. 3) or a DNA microarray (see FIG. 4) and the like, and comparing the expression profile thereof with the gene expression profile in ES cells (for example, fertilized egg-derived ES cells, ES cells derived from a clone embryo obtained by somatic cell nuclear transplantation from an NKT cell, and the like). To ensure higher accuracy, it is possible to transplant the selected cells to a mouse and confirm the formation of teratomas.

Figure 2:
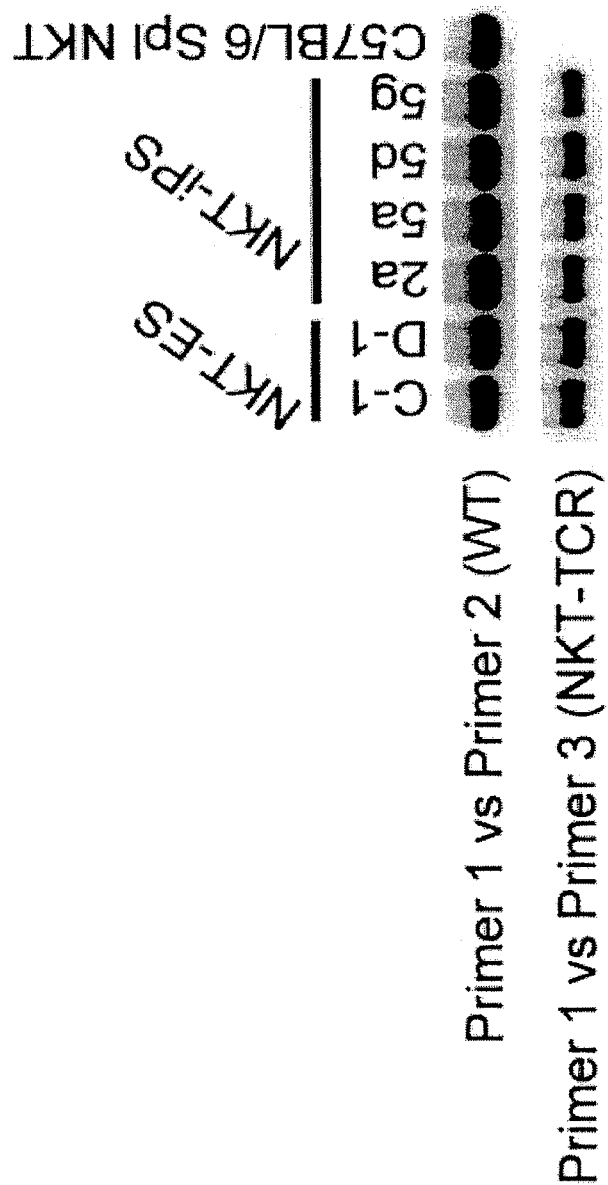
FIG. 2 is a drawing showing Vα-Jα rearrangement in NKT-iPS cells.

Confirmation of the fact that the NKT-iPS cells are derived from a somatic cell, such as an NKT cell, having the α chain region of the TCR gene (TCRα) is rearranged to uniform Vα-Jα in an NKT cell receptor-specific way can be achieved by examining the presence or absence of gene rearrangement to NKT-TCR (see FIG. 1) by genomic PCR, as described in Example 2 below (see FIG. 2).

The NKT-iPS cells thus established can be used for various purposes. For example, by utilizing a method of differentiation induction reported to have been applied to ES cells, hematopoietic stem cells and the like, differentiation into various cells (e.g., hematopoietic-immune system cells such as B cells, plasma cells, T cells, NK cells, NKT cells, neutrophils, eosinophils, basophils, mast cells, and macrophages, cardiac muscle cells, retinal cells, nerve cells, vascular endothelial cells, insulin-secreting cells and the like), tissues, and organs from NKT-iPS cells can be induced. For example, by culturing the NKT-iPS cells in the presence of cytokines such as IL-7 and an Flt3 ligand, with stromal cells that express a Notch ligand as feeder cells, on the basis of a report on ES cells, the NKT-iPS cells can be differentiated into CD4/CD8-double positive NKT cells. Furthermore, the NKT-iPS cells can be differentiated into functional mature NKT cells in vitro using the method described below.

In a preferred embodiment, the NKT-iPS cells are differentiated into functional mature or immature NKT cells, which are activated by stimulation with α-GalCer, ex vivo for utilization as, for example, a source of NKT cell immunotherapy agent. Therefore, the present invention also provides a method of generating an NKT cell by culturing an NKT-iPS cell under given conditions, and a mature or immature isolated NKT cell that can be obtained by the method.

First, CD4/CD8-double positive NKT cells (hereinafter also referred to as "DP-NKT cells") can be generated by co-culturing an NKT-iPS cell with stromal cells that express a Notch ligand. The stromal cells include, but are not limited to, OP9 cells, S17 cells and the like wherein a Notch ligand (e.g., Delta-like 1; hereinafter also referred to as "Dll-1") has been expressed forcibly. Examples of the medium for differentiation induction include, but are not limited to, a minimal essential medium (MEM), Dulbecco's modified Eagle medium (DMEM), RPMI1640 medium, 199 medium, and F12 medium containing cytokines such as interleukin-2 (IL-2), IL-7, IL-15, stem cell factor (SCF), and an Flt3 ligand (FL) (0.1-10 ng/mL each, preferably 1-5 ng/mL) and about 5 to 20% fetal bovine serum, and the like. NKT-iPS cells are seeded to obtain a cell density of, for example, about $1.0 \times 10^6$ to about $1.0 \times 10^7$ cells/mL, are cultured in a culture vessel known per se in an atmosphere of 5% $CO_2$/95% air, at about 30 to about 40° C., preferably at about 37° C., for about 1 to about 4 weeks, preferably for about 2 to about 3 weeks. Confirmation of their differentiation into DP-NKT cells can be achieved by, for example, analyzing the phenotype of a cell surface antigen using antibodies against CD4 and CD8 and a cell sorter (see FIG. 7). As required, it is also possible to examine the expression of still other various cell surface antigens, and compare the phenotype thereof with that of, for example, $CD4^+/CD8^+$ cells which are present in the thymus (see FIG. 8).

Figure 10:
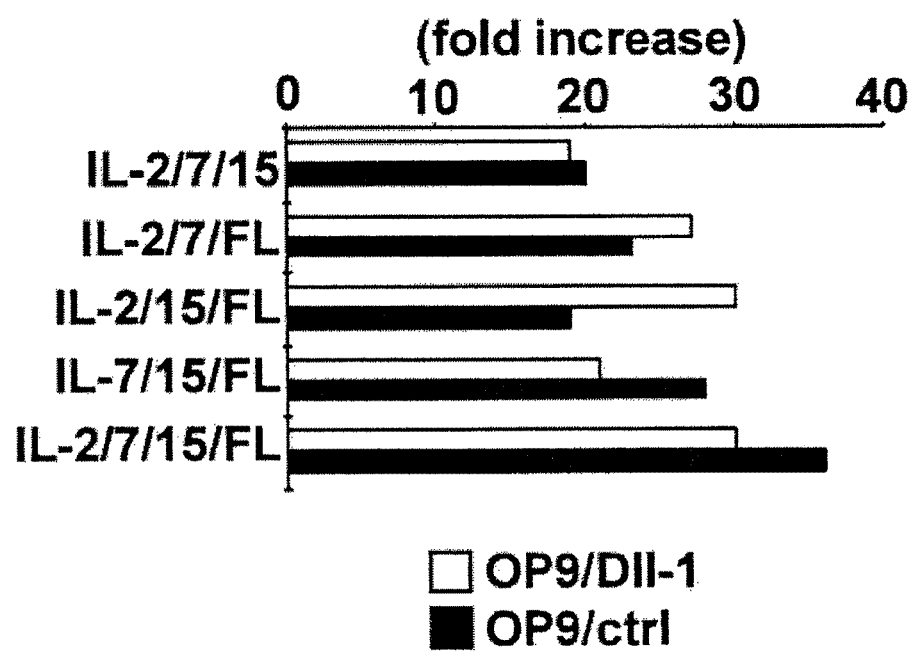
FIG. 10 is a drawing showing the mass expansion of NKT cells from DP-NKT cells using various combinations of cytokines.

By co-culturing DP-NKT cells obtained as described above with stromal cells in the presence of three or more cytokines selected from among IL-2, IL-7, IL-15 and FL, NKT cells can be expanded in large amounts (see FIG. 10). Although the stromal cells used in this operation include, for example, the same as the above, such as OP9 cells and S17 cells, the cells may or may not be expressing a Notch ligand. Preferred media are the same as those shown above except for the combinations of cytokines. Specific combinations of cytokines include IL-2/IL-7/IL-15, IL-2/IL-7/FL, IL-2/IL-15/FL, IL-7/IL-15/FL, and IL-2/IL-7/IL-15/FL; the combinations IL-2/IL-15/FL and IL-2/IL-7/IL-15/FL are particularly preferable. The concentration of each cytokine can be chosen as appropriate over the range of 0.1-10 ng/mL, preferably 1-5 ng/mL. Still another cytokine (e.g., SCF and the like) may be added to the medium. The cultivation is performed in an atmosphere of 5% $CO_2$/95% air at about 30 to about 40° C., preferably at about 37° C., for about 3 days to about 4 weeks, preferably for about 5 days to about 3 weeks. This cultivation allows the cell quantity to increase about 20 to about 30 times or more in 5 days.

Meanwhile, by co-culturing DP-NKT cells obtained as described above with stromal cells that do not express a Notch ligand, NKT cells that are very similar to peripheral NKT cells can be generated. These NKT cells are characterized by NK1.1-positivity, and further by phenotypes such as $CD3\epsilon^+$, $Sca1^+$, $CD44^+$, $CD69^+$, $CD34^-$, and $Flt3^-$ (see FIG. 9), with the expression of Vα14 (Vα24 in humans) decreased compared with DP-NKT cells, and showing expression levels equivalent to those in peripheral NKT cells (FIG. 11). In other words, by switching the feeder cells from stromal cells that express a Notch ligand to stromal cells that do not express the ligand, in the midst of cultivation for differentiation induction from NKT-iPS cells to DP-NKT cells, the NKT-iPS cells can be differentiated and matured into NKT cells that are equivalent to peripheral NKT cells. Examples of stromal cells that do not express a Notch ligand include, but are not limited to, OP9 cells, S17 cells, and the like. Although a medium for use for differentiation-induction from NKT-iPS cells to DP-NKT cells can be used likewise, it is preferable that the medium contain two or more cytokines selected from among IL-2, IL-7, IL-15 and FL, more preferably containing IL-15 (see FIG. 11). The timing of switching the feeder cells from stromal cells that express a Notch ligand to stromal cells that do not express the ligand is not particularly limited, as far as NKT cells equivalent to peripheral NKT cells (e.g., NK1.1-positive cells) are finally obtained; for example, about 12 to about 20 days after, preferably about 14 to about 18 days after starting co-cultivation of NKT-iPS cells and stromal cells that express a Notch ligand, the feeder cells are switched to stromal cells that do not express the ligand. The duration of co-cultivation with the stromal cells that do not express the Notch ligand is also not particularly limited; for example, the duration is about 3 days to about 4 weeks, preferably about 5 days to about 3 weeks. By performing this cultivation using a medium containing three or more cytokines selected from among IL-2, IL-7, IL-15 and FL (preferably one thereof is IL-15), NKT cells that have differentiated and matured to the same extent as with peripheral NKT cells can be acquired in large amounts.

Because the NKT-iPS cell-derived NKT cells obtained as described above (hereinafter also referred to as "iPS-NKT cells") are CD1d-restricted, iPS-NKT cells can be activated by contacting these cells with α-GalCer-presenting dendritic cell (DC). The DC is preferably derived from the same species as the iPS-NKT cells, a heterologous DC may be used, as far as the iPS-NKT cells can be activated (for example, contacting human DC and mouse iPS-NKT cells). The DC is not particularly limited, as far as it is capable of activating iPS-NKT cells via α-GalCer; although the DC may be a myeloid lineage dendritic cell (DC1) or a lymphoid dendritic cell (DC2), DC1 is preferred. The DC may be generated by any method known per se, and can be separated from the bone marrow, peripheral non-lymphatic tissue, the T cell region of lymphatic tissue, afferent lymph, epidermis, dermis and the like; preferably, the DC can be generated by separating monocytes, myelocytes and the like from bone marrow cells, peripheral blood and the like, for example, by density gradient centrifugation and the like, and culturing the cells in the presence of GM-CSF (and IL-4) for about 7 to about 10 days.

In the present invention, it is understood that the α-GalCer used to pulse DC encompasses not only α-galactosyl ceramide or salts thereof or esters thereof and the like, but also an optionally chosen derivative thereof capable of binding to CD1d to activate DC and being antigen-presented to NKT cells (for example, synthetic lipids with a shortened fat chain, such as OCH, and the like). These can be synthesized by a method known per se. When the DC-activated iPS-NKT cells are intended to be administered to humans, the α-GalCer used to pulse DC is desirably of GMP grade. Pulsation of DC with α-GalCer can be performed by a technique in common use; for example, the pulsation can be performed by culturing the DC in a serum-containing medium (for example, 10% FCS-containing RPMI-1640 medium and the like) containing α-GalCer at a concentration of about 0.1 to about 200 ng/mL for about 12 to about 48 hours. The pulsation with α-GalCer may be performed by adding α-GalCer to the medium in the process of culturing and maturing the immature DC in the presence of GM-CSF (and IL-4). Alternatively, the pulsation may be performed by adding α-GalCer to the medium in the step of co-culturing the DC matured as described below with iPS-NKT cells.

Contact of the DC and iPS-NKT cells can be achieved by, for example, co-culturing both in the above-described medium in differentiation-induction from NKT-iPS cells to iPS-NKT cells exhibiting phenotypes equivalent to those of peripheral NKT cells.

Herein, "an activated NKT cell" means an iPS-NKT cell that at least produces a Th1 cytokine such as IFN-γ in response to α-GalCer-presenting DC. The cell may further possess productivity for a Th2 cytokine such as IL-4, and may possess a proliferation potential. For iPS-NKT cells to acquire a proliferation potential and Th2 cytokine productivity as well upon stimulation with α-GalCer-presenting DC, the cells need to continue to be co-cultured with stromal cells that express a Notch ligand in the process of differentiation induction from NKT-iPS cells to iPS-NKT cells; in this case, the IFN-γ productivity also increases compared with iPS-NKT cells obtained by switching to stromal cells that do not express a Notch ligand (see FIG. 12). By choosing the combination IL-2/IL-15/FL as cytokines in the culturing step for mass expanding iPS-NKT cells from DP-NKT cells, the Th1/Th2 cytokine production balance in activated NKT cells, in particular, exhibits Th1 dominance (see FIG. 12).

The present invention also provides an NKT cell cytotherapy agent comprising activated NKT cells obtained as described above. The activated NKT cells provided by the present invention possess a proliferation potential and Th1-dominant cytokine productivity, and are therefore useful in, for example, preventing/treating various diseases such as cancers, infectious diseases, and allergic diseases. As the cancers, all kinds of primary cancers can be mentioned, and all conditions of cancers, including early cancers and advanced cancers with a metastatic/infiltrating potential, can be mentioned.

The activated NKT cells are produced as an oral/parenteral preparation, preferably as an injection, suspension, or drip infusion, by being blended with a pharmaceutically acceptable carrier by a conventional means or otherwise. Pharmaceutically acceptable carriers that can be contained in the parenteral preparation include, for example, aqueous solutions for injection, such as physiological saline and isotonic solutions containing glucose or another auxiliary drug (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative, an antioxidant and the like.

When the agent of the present invention is prepared as an aqueous suspension, the activated NKT cells are suspended in the above-described aqueous liquid to about $1.0 \times 10^6$ to $1.0 \times 10^7$ cells/ml.

Because the preparation thus obtained is stable and of low toxicity, it can be safely administered to mammals such as humans. Although the recipient of administration is preferably the patient from which the NKT cells used as the starting material for generating the NKT-iPS cells are derived (that is, autologous transplantation); however, this is not to be construed as limiting, as far as the source is another individual of the same species that is estimated to be compatible to the activated NKT cells administered (that is, shares the same HLA type). Although the method of administration is not particularly limited, the preparation can be administered orally or parenterally, preferably by injection or drip infusion; examples include intravenous administration, subcutaneous administration, intradermal administration, intramuscular administration, intraperitoneal administration, direct administration to the affected site and the like. The dose of the NKT cell cytotherapy agent varies depending on the recipient of administration, target organ, symptoms, method of administration and the like; in the case of parenteral administration, for example, it is normally convenient to administer about $1.0 \times 10^5$ to about $1.0 \times 10^7$ cells, based on the amount of activated NKT cells per dose, at intervals of about 1 to about 2 weeks, about 4 to about 8 times, for an adult patient (assuming a body weight of 60 kg).

The present invention also provides an NKT cell cytotherapy agent comprising iPS-NKT cells obtained as described above and α-GalCer in combination. The iPS-NKT cells provided by the present invention function like endogenous NKT cells to exhibit an adjuvant effect when administered to a mammal such as a human, and are therefore useful in, for example, preventing/treating various diseases such as cancers, infectious diseases, and allergic diseases. As the cancers, all kinds of primary cancers can be mentioned, and all conditions of cancers, including early cancers and advanced cancers with a metastatic/infiltrating potential, can be mentioned.

The iPS-NKT cells can be produced as an oral/parenteral preparation, preferably as a parenteral preparation such as an injection, suspension, or drip infusion, by being blended with a pharmaceutically acceptable carrier in the same manner as in the above-described case of activated NKT cells, and can be administered with the same doses and routes of administration.

As the α-GalCer for use in combination with the iPS-NKT cells, the same as the above described with respect to the generation of activated NKT cells can be used; however, when the recipient of administration is a human, α-GalCer of GMP grade is used. In patients suffering a disease that requires NKT cell cytotherapy, such as a cancer, who sometimes have a decreased number or lacked function of endogenous DC, α-GalCer-pulsed DC may be used in place of α-GalCer to improve the activation of the iPS-NKT cells in vivo. In this case, the source of DC collected is preferably the patient who is the recipient of administration (that is, autologous transplantation); however, this is not to be construed as limiting, as far as the source is another individual of the same species that is estimated to be compatible to the patient (that is, shares the same HLA type).

The α-GalCer is normally produced, along with a pharmaceutically acceptable carrier, as a parenteral preparation such as an injection, suspension, or drip infusion. Pharmaceutically acceptable carriers that can be contained in the parenteral preparation include, for example, aqueous solutions for injection, such as physiological saline and isotonic solutions containing glucose or another auxiliary drug (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., benzalkonium chloride, procaine hydrochloride and the like), a stabilizer (e.g., human serum albumin, polyethylene glycol and the like), a preservative, an antioxidant and the like. When the α-GalCer is prepared as an aqueous suspension, the α-GalCer is dissolved in an appropriate organic solvent (e.g., DMSO and the like) and dissolved in the above-described aqueous liquid to obtain a cell density of about 100 μg to about 1 mg/mL.

Meanwhile, when using α-GalCer-pulsed DC in place of α-GalCer, α-GalCer-pulsed DC prepared by the technique described above with respect to generating activated NKT cells may be suspended in the above-described aqueous liquid to about $1.0 \times 10^6$ to about $1.0 \times 10^7$ cells/mL.

The α-GalCer prepared as a preparation as described above can be administered orally or parenterally, preferably by injection or drip infusion; examples include intravenous administration, subcutaneous administration, intradermal administration, intramuscular administration, intraperitoneal administration, direct administration to the affected site and the like. The dose of the α-GalCer varies depending on the recipient of administration, target organ, symptoms, method of administration and the like; in the case of parenteral administration, for example, the dose is normally about 0.6 to about 6.0 mg, based on a single dose, for an adult patient (assuming a body weight of 60 kg). Meanwhile, when using α-GalCer-pulsed DC in place of α-GalCer, the dose thereof is normally about $1.0 \times 10^5$ to about $1.0 \times 10^7$ cells per dose. These amounts can be administered according to the administration protocol for the iPS-NKT cell-containing preparation.

The iPS-NKT cell-containing preparation and the α-GalCer-containing preparation may be administered simultaneously separately or as blended just before use, and may be administered sequentially in the order of the iPS-NKT cell-containing preparation and then the α-GalCer-containing preparation.

The present invention is hereinafter described in more detail by means of the following Examples, to which, however, the invention is not limited in any way.

EXAMPLES

Example 1

Establishment of iPS Cells from Mouse splenocyte-Derived NKT Cells

NKT cells were prepared from splenocytes of a C57BL/6 mouse having the T cell antigen receptor α-chain (TCRα) region already rearranged to TCR used in NKT cells (NKT-TCR). Since NKT cells are characterized by recognizing glycolipid antigens presented to the MHC class I-like molecule CD1d, the cells were concentrated by positively selecting cells reactive to an anti-mouse IgG1 antibody prepared by APC-labeling a solubilized CD1d-mouse IgG1 recombinant having the glycolipid antigen α-GalCer inserted therein (produced by BD Bioscience Company), using a MACS method which utilizes anti-APC magnetic beads (produced by Miltenyi Biotech Company). This operation rendered the NKT cells as defined as α-GalCer loaded CD1d dimer-positive/TCRβ-positive cells to have a purity of 90% or more. The concentrated NKT cells were cultured in the presence of IL-2 (10 ng/ml) at a cell density of $10^6$ cells/ml, using an RPMI medium containing 10% FCS for 24 hours, after which the cells were infected with a retrovirus containing four mouse-derived factors (nucleic acids that encode Oct3/4, Sox2, Klf4, and c-Myc) ($10^6$ pfu/ml) according to the method described in Cell, 126: 663-676 (2006) for 24 hours. Three to seven days after the viral infection, the cells were recovered, re-seeded onto mouse embryonic fibroblasts (MEF), and co-cultured in the presence of LIF using an ES cell culture medium. The emerging colonies were morphologically evaluated, and colonies assuming an ES-like morphology were picked up and further cultured in the presence of LIF on MEF, whereby 4 clones of NKT cell-derived iPS cells (NKT-iPS cells) were established (clone code names: 2a, 5b, 5d, 5g).

Example 2

Characterization of NKT-iPS Cells

To demonstrate that the four clones of NKT-iPS cells established in Example 1 were derived from NKT cells, whether rearrangement to NKT-TCR had occurred was determined by genomic PCR. In the cells having NKT-TCR, either TCRα region had already been rearranged to Vα14-Jα18 (FIG. 1); hence, the presence or absence of rearrangement was checked by performing a PCR using the primers shown below with the genome of each NKT-iPS clone as the template.

```
SEQ ID NO: 1:
Primer 1: 5'-gacccaagtggagcagagtcct-3'

SEQ ID NO: 2:
Primer 2: 5'-tcacctatgtctcctggaagcctc-3'

SEQ ID NO: 3:
Primer 3: 5'-cagctccaaaatgcagcctccctaa-3'
```

[In case where rearrangement to Vα14-Jα18 has not occurred (wild), a 349 bp band is amplified by a PCR using primer 1 and primer 2; meanwhile, in case where rearrangement to Vα14-Jα18 has occurred (NKT-TCR), a 317 bp band is amplified by a PCR using primer 1 and primer 3.]

As a result, all of the four established clones were found to have either genome rearranged to NKT-TCR (FIG. 2), confirming that the established iPS cells were of NKT cell derivation.

Example 3

Genetic Expression Analysis of NKT-iPS Cells

To determine whether the NKT-iPS cells identified in Example 2 had been reprogrammed to iPS-like cells, gene expression profiling was performed. Total RNA was prepared from each of NKT-iPS cells, NKT cell nuclear transplantation embryo-derived ES cells (NKT-ES cells), and peripheral NKT cells by the phenol-chloroform method, the expression of a series of gene groups whose expression in ES cells is known was analyzed by the one step RT-PCR method (produced by Invitrogen Company). The genes analyzed and the sequences of the primers used are shown below.

```
Endogenous Oct3/4:
(SEQ ID NO: 4)
5'-tctttccaccaggcccccggctc-3'

(SEQ ID NO: 5)
5'-tgcgggcggacatggggagatcc-3'

Endogenous Sox2:
(SEQ ID NO: 6)
5'-tagagctagactccgggcgatga-3'

(SEQ ID NO: 7)
5'-ttgccttaaacaagaccacgaaa-3'

Endogenous Klf4:
(SEQ ID NO: 8)
5'-gcgaactcacacaggcgagaaacc-3'

(SEQ ID NO: 9)
5'-tcgcttcctcttcctccgacaca-3'

Endogenous c-Myc:
(SEQ ID NO: 10)
5'-tgacctaactcgaggaggagctggaatc-3'

(SEQ ID NO: 11)
5'-aagtttgaggcagttaaaattatggctgaagc-3'

Ecat1:
(SEQ ID NO: 12)
5'-tgtggggccctgaaaggcgagctgagat-3'

(SEQ ID NO:13)
5'-atgggccgccatacgacgacgctcaact-3'

Nanog:
(SEQ ID NO: 14)
5'-caggtgtttgagggtagctc-3'

(SEQ ID NO: 15)
5'-cggttcatcatggtacagtc-3'

Gdf3:
(SEQ ID NO: 16)
5'-gttccaacctgtgcctcgcgtctt-3'

(SEQ ID NO :17)
5'-agcgaggcatggagagagcggagcag-3'

Rex1:
(SEQ ID NO: 18)
5'-acgagtggcagtttcttcttggga-3'

(SEQ ID NO: 19)
5'-tatgactcacttccaggggcact-3'

Zfp296:
(SEQ ID NO: 20)
5'-ccattaggggccatcatcgctttc-3'

(SEQ ID NO: 21)
5'-cactgctcactggaggggggcttgc-3'

HPRT:
(SEQ ID NO: 22)
5'-ctgtgtgctcaagggggggct-3'

(SEQ ID NO: 23)
5'-ggactcctcgtatttgcagattcaacttg-3'
```

Figure 3:
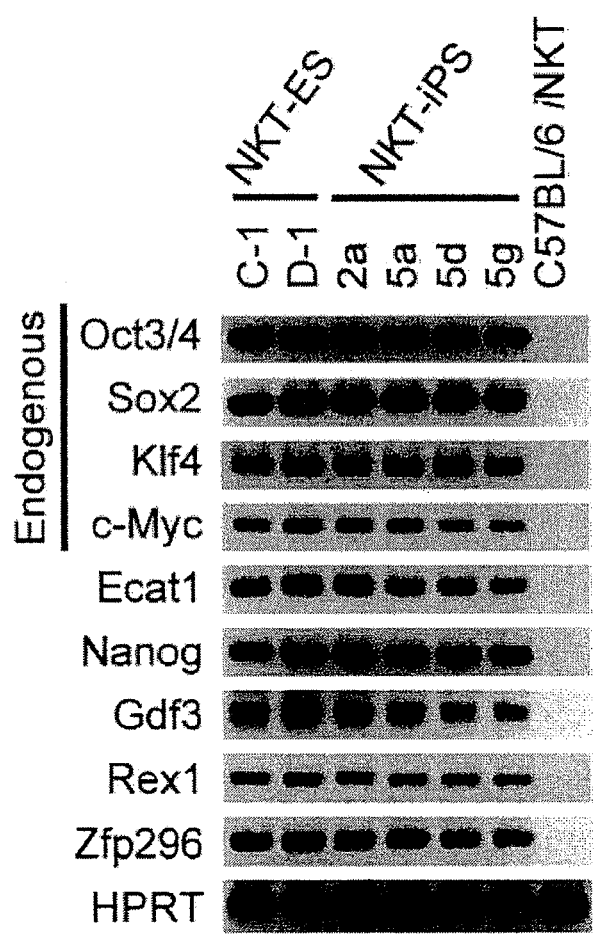
FIG. 3 is a drawing showing the expression of ES cell-specific genes in NKT-iPS cells.

As a result, the expression of all of the genes analyzed was confirmed in NKT-iPS cells and NKT-ES cells, but no expression was confirmed in peripheral NKT cells (FIG. 3). This result suggests that the established NKT-iPS cells may possess an iPS cell-like function.

Figure 4:
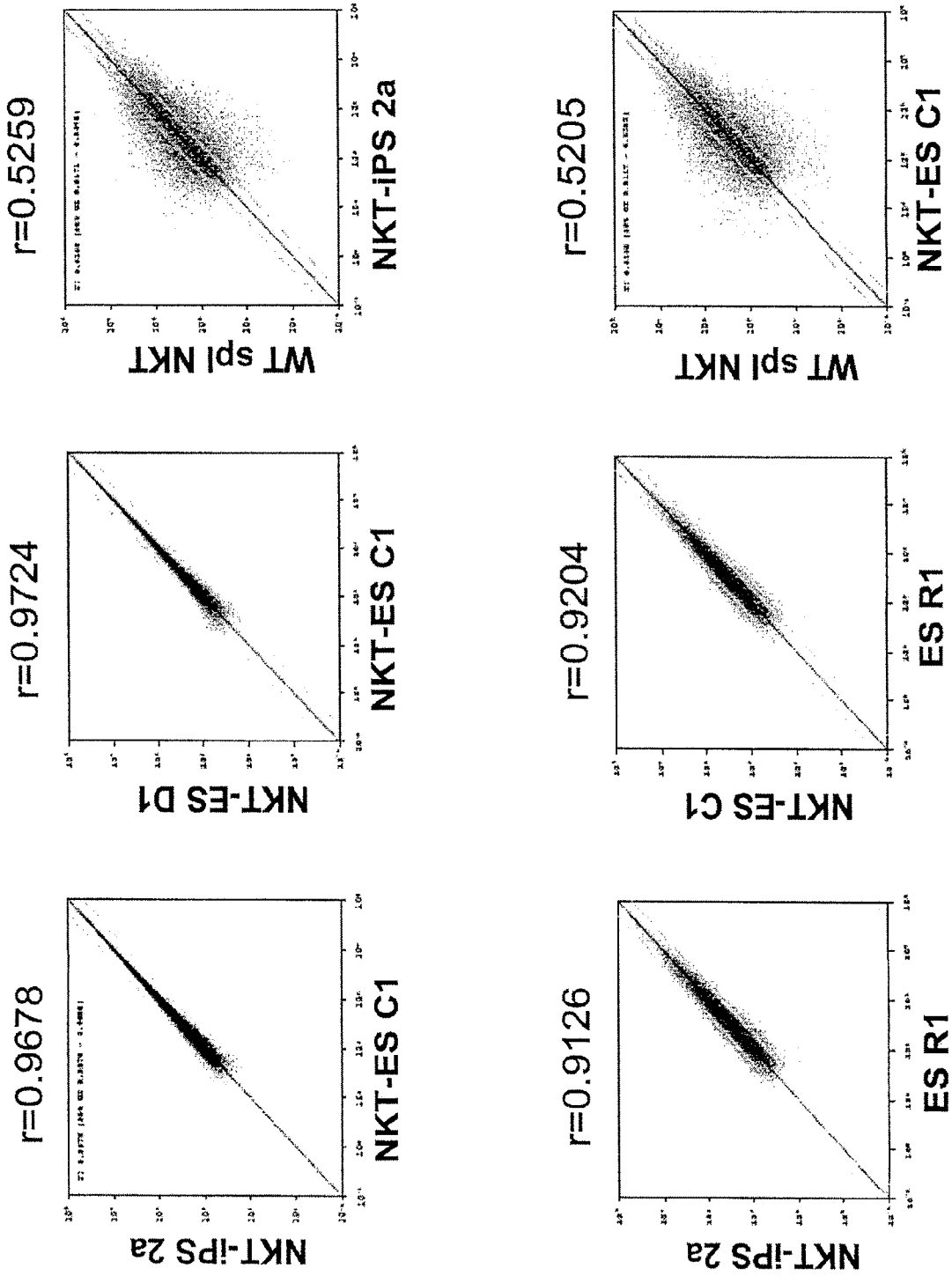
FIG. 4 is a drawing showing the correlations of gene expression profiles between NKT-iPS cells and NKT-ES cells or ES cells, and between NKT-iPS cells and wild type spleen NKT cells.

Furthermore, using a DNA microarray (produced by Affimetrix Company), gene expression profile correlations were checked among NKT-iPS cells, NKT-ES cells, ES cells, and peripheral NKT cells; it was found that the NKT-iPS cells had a gene expression pattern very similar to that of the NKT-ES cells or the ES cells, being distinct from the peripheral NKT cells (FIG. 4).

Example 4

Morphological Examination of NKT-iPS Cells

Figure 5:
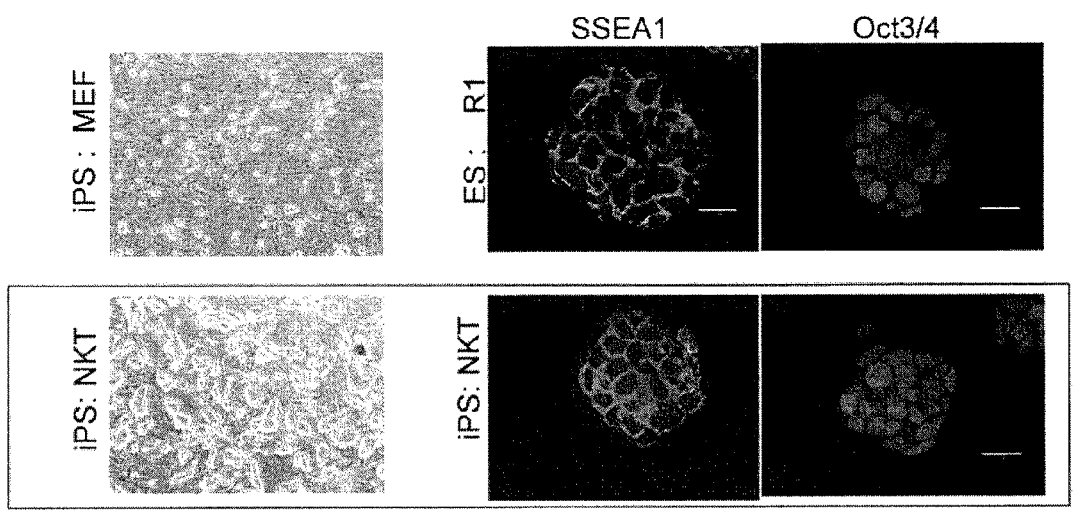
FIG. 5 is a drawing showing the similarity of NKT-iPS cells to MEF-derived iPS cells or ES cells in morphology and the expression of the SSEA1 and Oct3/4 genes.

The morphology of the NKT-iPS cells established in Example 2 was examined under a microscope. As a result, it was demonstrated that the localized expression of SSEA1 and Oct3/4 and the morphology of the NKT-iPS cells were very similar to those of ES cells (FIG. 5).

Example 5

Establishment and Analysis of NKT-iPS Chimeric Mouse

Figure 6:
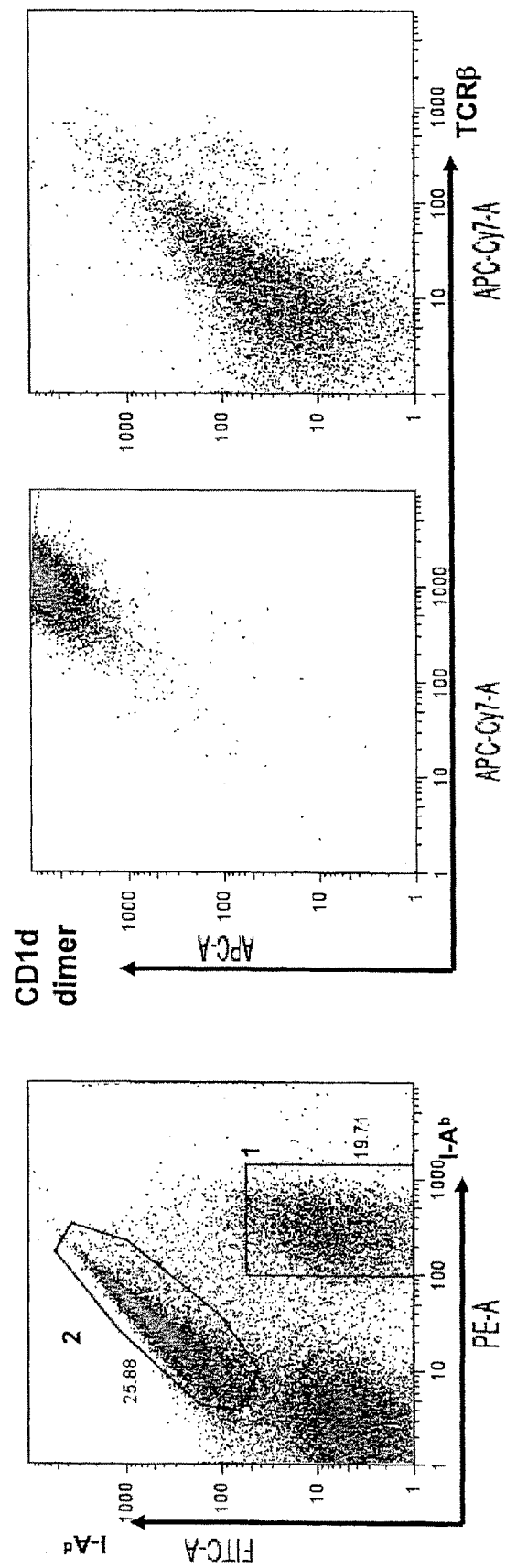
FIG. 6 is a drawing showing how TCRα/β is expressed in each mouse derived cell in splenocytes of an NKT-iPS chimeric mouse generated from a C57BL/6 mouse derived NKT-iPS cell clones 2a and a Balb/C mouse-derived cell.

A chimeric mouse was generated from an NKT-iPS cell derived from the C57BL/6 mouse NKT clone established in Example 2 and a Balb/c-derived cell by the aggregation method. Splenocytes of the chimeric mouse obtained were analyzed for cell surface antigens. C57BL/6-derived cells and Balb/c-derived cells were gated by distinction by MHC class I (I-$A^b$ and I-$A^d$, respectively), and the NKT cell content ratios were analyzed. As a result, almost all of the C57BL/6-derived cells had a surface antigen like that of α-GalCer loaded CD1d dimer-positive/TCRβ-positive NKT cells, whereas the Balb/c-derived cells contained T/NKT cells at an ordinary frequency (FIG. 6).

Example 6

In Vitro Differentiation Induction from NKT-iPS Cells

Figure 7:
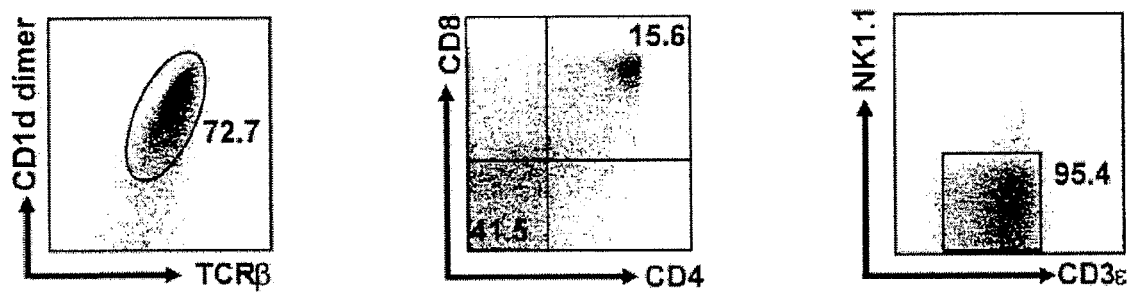
FIG. 7 is a drawing showing the in vitro differentiation induction of DP-NKT cells from NKT-iPS cells.
Figure 8:
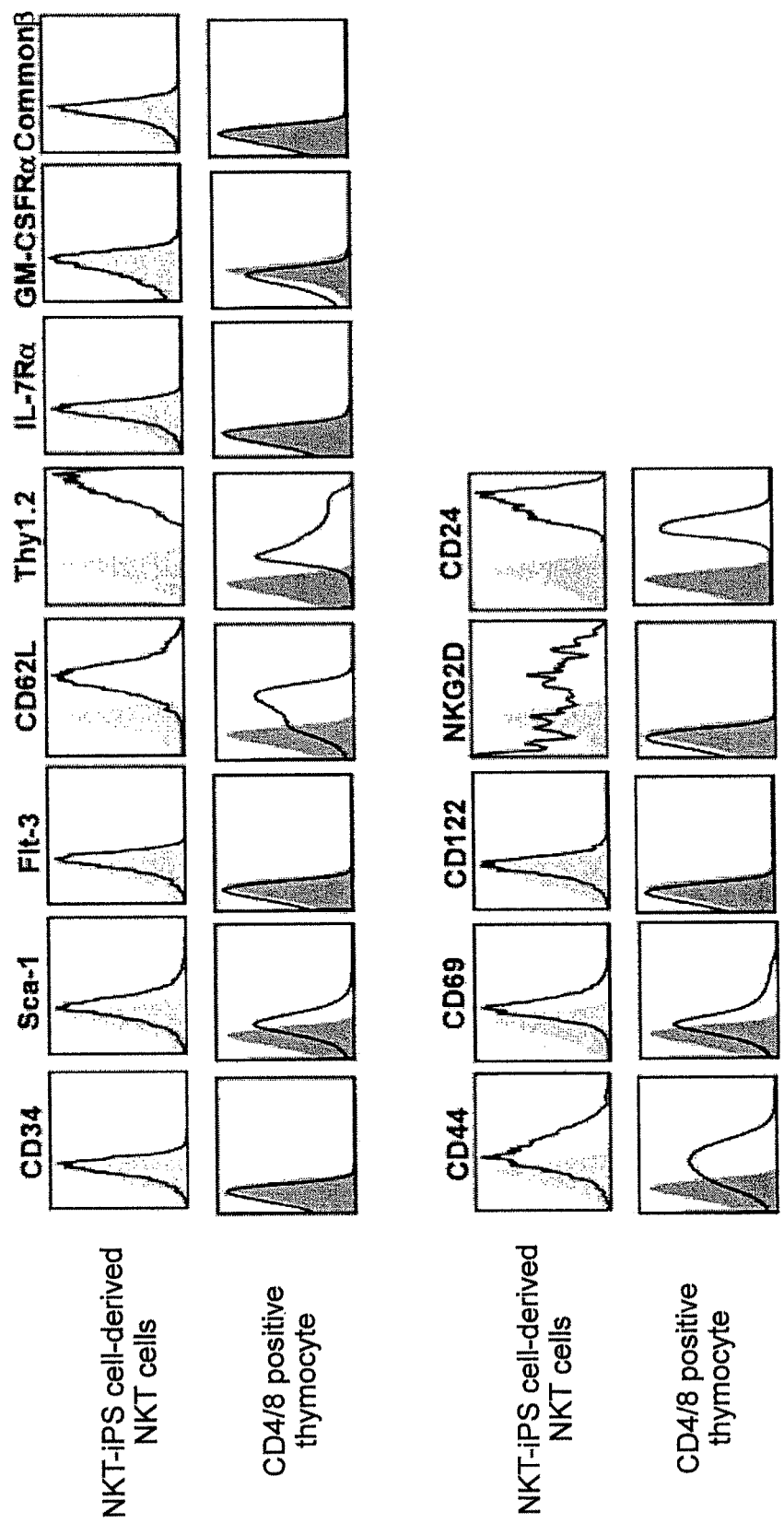
FIG. 8 is a drawing showing results of a phenotype analysis of DP-NKT cells.

ES cells can be differentiation-induced into CD4/CD8-double positive (DP) T cells by being co-cultured with OP9 stromal cells forcibly expressing the Notch ligand Delta-like 1 (Dll-1) (OP9/Dll-1) in the presence of IL-7 and an Flt3 ligand (FL) (Schmitt T M, de Pooter R F, Gronski M A, Cho S K, Ohashi P S, Zuniga-Pflucker J C. Induction of T cell development and establishment of T cell competence from embryonic stem cells differentiated in vitro. Nat. Immunol. 2004 April; 5(4):410-417). On the basis of this finding, NKT-iPS cells were co-cultured with OP9/Dll-1 cells in the presence of IL-7 (1 ng/ml) and FL (5 ng/ml) for 20 days; it was demonstrated that CD4/CD8 DP α-GalCer loaded CD1d dimer-positive/TCRβ-positive NKT cell-like cells (NKT-iPS cell-derived DP-NKT cells) would be induced (FIG. 7). A cell surface antigen expression analysis was performed in more detail, demonstrating that the phenotype of the DP-NKT cells is very similar to that of CD4/CD8 DP cells in the thymus (FIG. 8). This result suggests that NKT-iPS cells, under the influence of TCRα region gene rearrangement, may be likely to undergo differentiation induction to NKT-like cells, and also shows that by introducing a new concept making the best use of the gene rearrangement in immune cells, it is possible to secure a technology for generating desired immune cells (particularly NKT cells, T cells, B cells) in large amounts.

Example 7

In Vitro Differentiation Induction of Mature NKT Cells from NKT-iPS Cells

Figure 9:
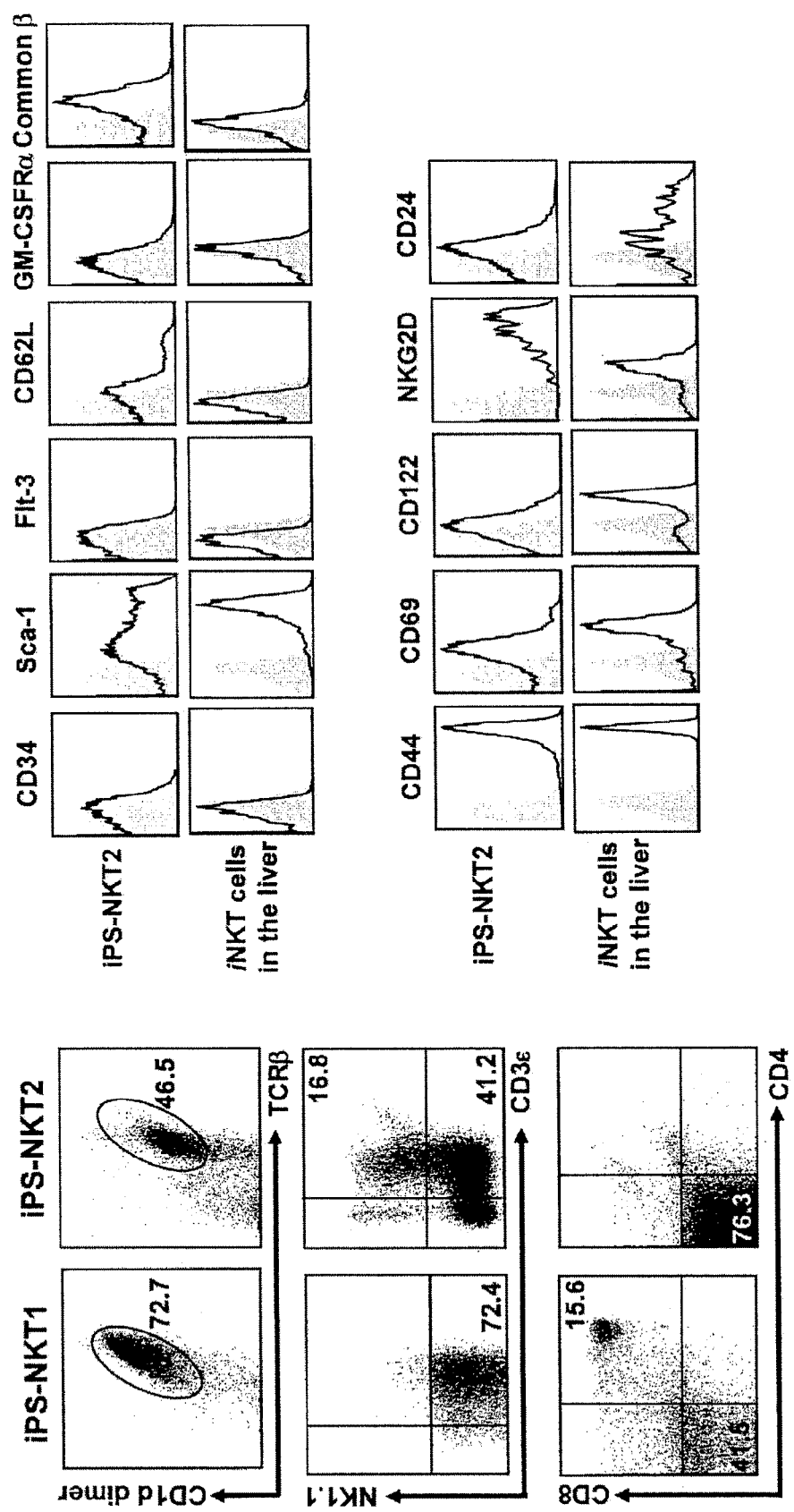
FIG. 9 is a drawing showing the in vitro differentiation induction of NKT cells that exhibit the same phenotype as peripheral NKT cells, from NKT-iPS cells.

An analysis was performed to determine whether NKT cells would be induced by co-culturing NKT-iPS cells with OP9/Dll-1 until day 14 of cultivation, and then with OP9 from day 14 to day 20 of cultivation. As a result, it was found that NKT cells could emerge even in an early differentiation stage wherein only what is called DN1, which is Lin-negative/CD44-positive/CD25-negative, had emerged (FIG. 9), and that the surface markers of the differentiation-induced NKT cells were very similar to those of peripheral NKT cells (FIG. 9). This result shows that NKT cells are capable of differentiating into mature NKT cells even if the Notch signal is lacked in an early differentiation stage.

Example 8

Figure 12:
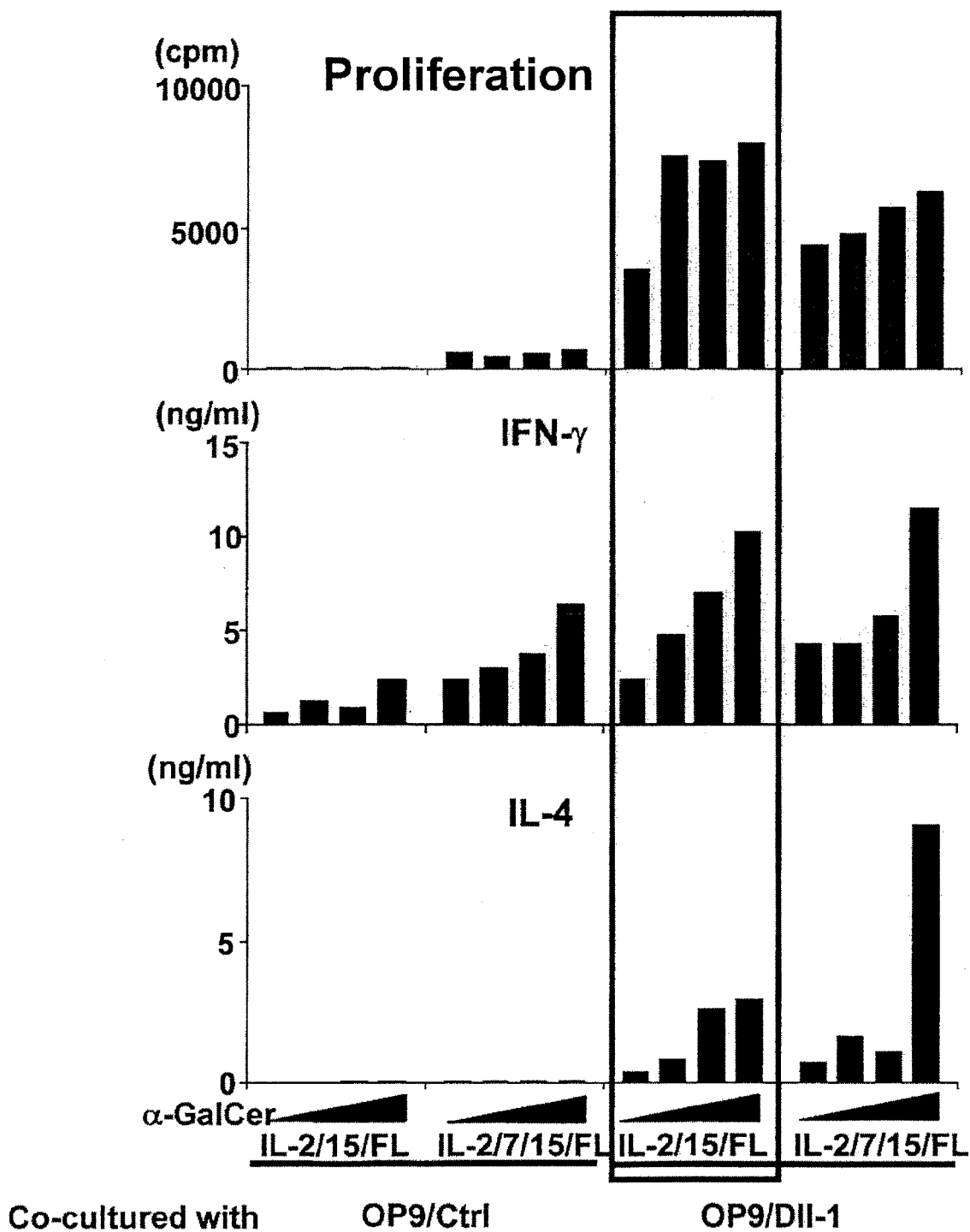
FIG. 12 is a drawing showing the α-GalCer responsiveness of NKT cells differentiation-induced from an NKT-iPS cell.

In Vitro Differentiation Induction of Mature NKT Cells from NKT-iPS Cell-Derived DP-NKT Cells To further expand and mature NKT-iPS cell-derived DP-NKT cells whose induction was confirmed in Example 6, in vitro, the cells were cultured using various combinations of cytokines with or without feeder cells for 5 days. As a result, it was demonstrated that by co-cultivation with OP9 or OP9/Dll-1 in the presence of the IL-2/IL-15/FL or IL-2/IL-7/IL-15/FL cytokine combination, the cells could be further expanded more than 10 times (FIG. 10). Furthermore, it was estimated that the cells cultured under these conditions had undergone further differentiation induction, with the expression of NK1.1 induced therein (FIG. 11). Hence, the NKT cells obtained by induction by co-cultivation with OP9 or OP9/Dll-1 in the presence of the IL-2/IL-15/FL or IL-2/IL-7/IL-15/FL cytokine combination were co-cultured with bone marrow cell-derived dendritic cells (induced with GM-CSF) in the presence of α-GalCer, whereby the proliferation potential and cytokine productivity thereof were checked. As a result, it was confirmed that a proliferation potential was observed when the cells were further cultured with OP9/Dll-1 (FIG. 12), and that a bias to Th1 existed particularly when cultured with IL-2/IL-15/FL (FIG. 12).

Example 9

Adjuvant Effect of NKT-iPS Cell-Derived Mature NKT Cells In Vivo

Figure 13:
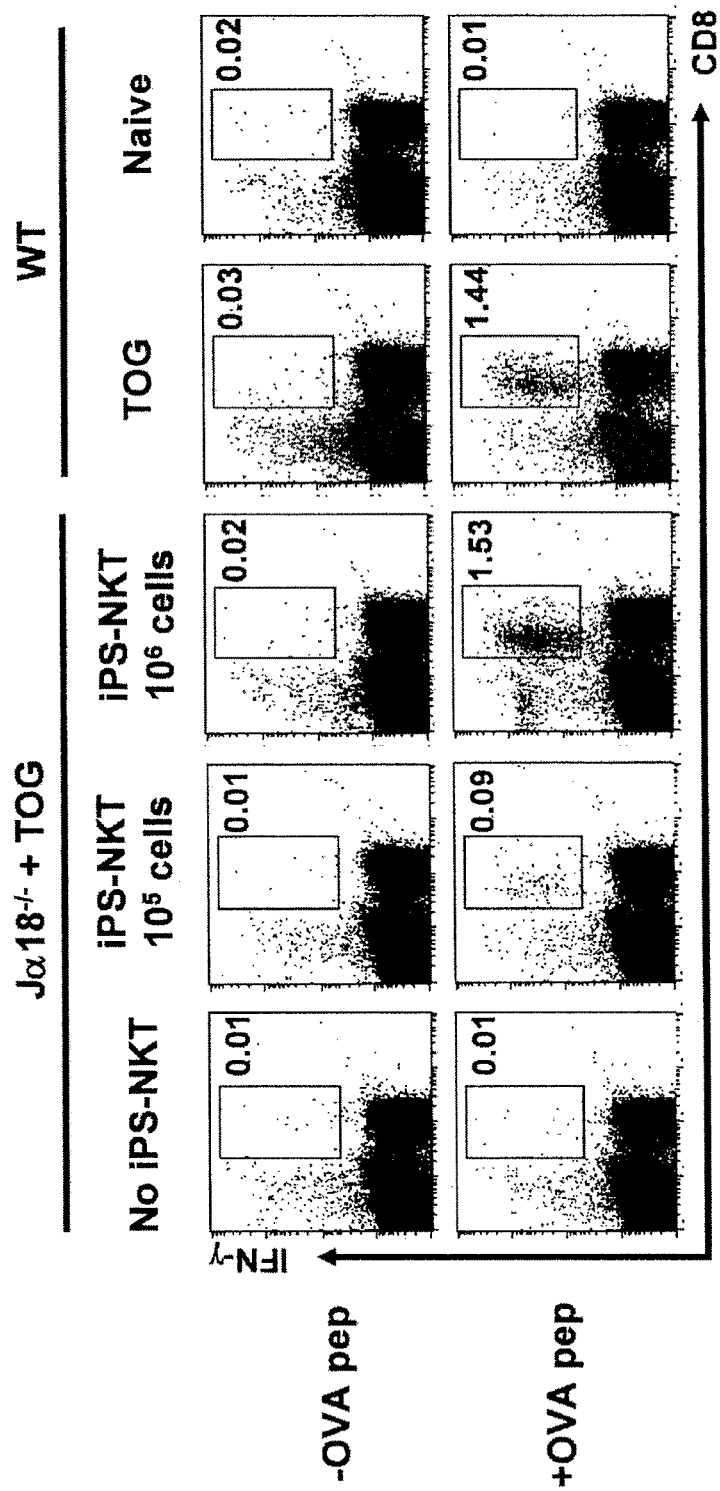
FIG. 13 is a drawing showing the in vivo adjuvant effect of NKT cells differentiation-induced from an NKT-iPS cell.

An evaluation was performed to determine whether the NKT-iPS cell-derived mature NKT cells induced in Example 8 (co-cultured with OP9/Dll-1 in the presence of IL-7/FL for 20 days, then with OP9/Dll-1 in the presence of IL-2/IL-15/FL for 5 days) were functional in vivo. TAP knockout mouse-derived splenocytes were cultured with 10 mg/ml ovalbumin (OVA) in a hypertonic solution, after which apoptosis was induced, and $2 \times 10^7$ apoptotic cells, along with 2 μg of α-GalCer, were transferred to a Jα18 knockout mouse (NKT cell-deficient mouse) having $10^5$ or $10^6$ NKT-iPS cell-derived mature NKT cells transferred in advance 1 hour previously. Seven days later, splenocytes were collected from the mouse, stimulated with OVA peptide (257-264) in vitro, and analyzed for IFN-γ production by intracellular staining. As a result, it was confirmed that OVA-antigen specific CD8-positive T cells possessing IFN-γ productivity had been induced dependently on the number of cells transferred, demonstrating that the NKT-iPS cell-derived mature NKT cells function in vivo and have a potent adjuvant effect (FIG. 13).

Example 10

Establishment of iPS Cells from Wild Mouse Splenocyte-Derived NKT Cells

Figure 14:
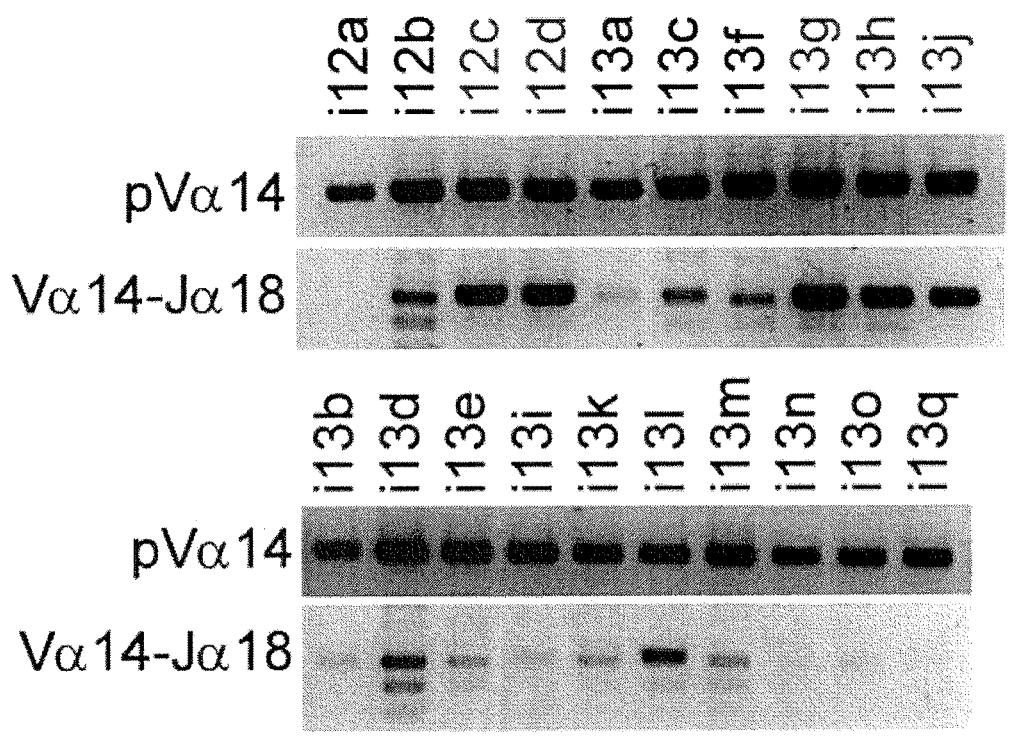
FIG. 14 is a drawing showing the establishment of an iPS cell from C57BL/6 wild mouse splenocytes.

In Examples 1-8, the establishment of NKT-iPS cells from a purified mouse NKT cell population, differentiation induction from the NKT-iPS cells to NKT cells, the possession by the cells of a function as NKT cells, and the like were demonstrated. Hence, by the same procedure as Example 1, NKT cells were prepared from splenocytes of a C57BL/6 mouse without a concentrating operation, whereby an NKT cell population of about 30-50% purity was obtained. These cells were cultured in the presence of IL-2 (10 ng/ml) at a cell density of $10^6$ cells/ml for 24 hours in the same manner as in Example 1, after which the cells were infected with a retrovirus containing four mouse-derived factors (nucleic acids that encode Oct3/4, Sox2, Klf4, and c-Myc) ($10^6$ pfu/ml) for 24 hours. Three to seven days after the viral infection, the cells were recovered, re-seeded onto mouse embryonic fibroblasts (MEF), and co-cultured in the presence of LIF using an ES cell culture medium. The emerging colonies were morphologically evaluated, and colonies assuming an ES-like morphology were picked up and further cultured in the presence of LIF on MEF, whereby 5 clones of NKT-iPS cells were successfully established (clone code name: i12c, i12d, i13g, i13h, i13i) (FIG. 14).

Generation Example 1

Generation of NKT Clone Mouse with C57BL/6 Background

Figure 15:
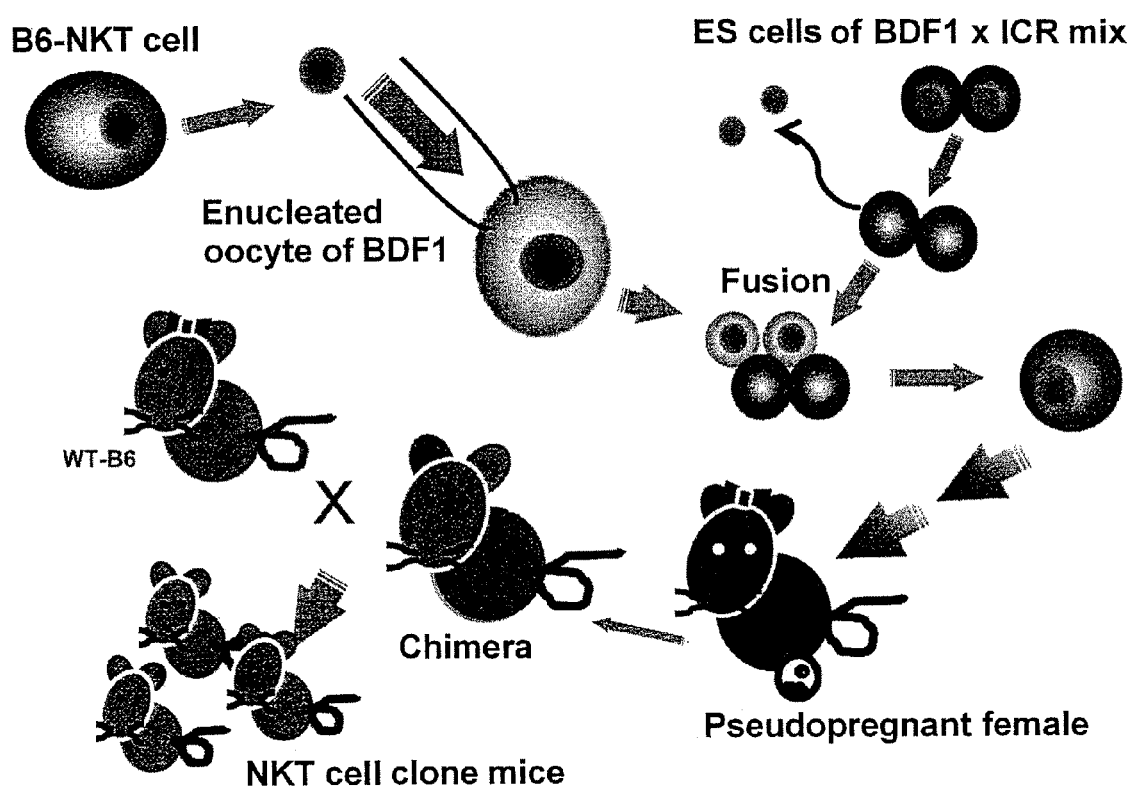
FIG. 15 is a drawing showing the generation of an NKT clone mouse with C57BL/6 background.

As shown in FIG. 15, for the purpose of performing a cell transfer experiment, an NKT clone mouse with C57BL/6 background was generated. That is, the nucleus of a C57BL/6 mouse spleen-derived NKT cell was transferred into an enucleated oocyte of a BDF1 mouse. This cell was fused with an ES cell of BDF1×ICR, transferred to the uterus of a foster mother, and an offspring chimeric mouse was obtained. The chimeric mouse (male) obtained was crossed with a C57BL/6 mouse (female), and the offspring obtained was used as the NKT clone mouse with C57BL/6 background.

In the NKT clone mouse established using this method, the starting nucleus was 100% derived from an NKT cell derived from the spleen of the C57BL/6 mouse; therefore, the clone mouse is a complete C57BL/6, and does not undergo an allogenic or semi-allogenic reaction with the C57BL/6 mouse. The only genomic difference between the NKT clone mouse with C57BL/6 background and the C57BL/6 mouse seems to be the difference in sequence due to T cell receptor region rearrangement as a result of the differentiation into NKT cells. The base sequence of the T cell receptor region of an NKT clone mouse with C57BL/6 background wherein rearrangement has completed is shown in FIG. 16.

Example 11

Figure 17:
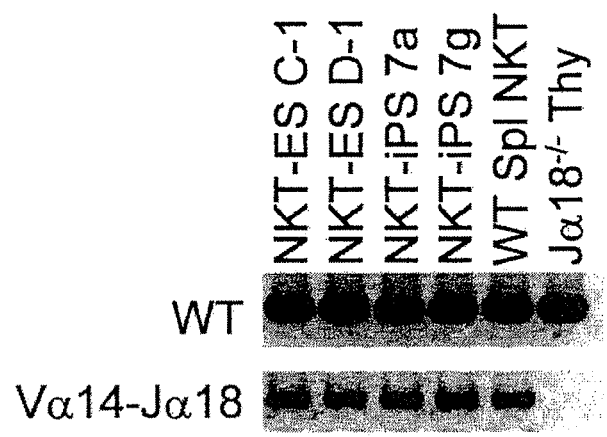
FIG. 17 is a drawing showing a gene rearrangement analysis of NKT-iPS cell clones 7a and 7g.
Figure 18:
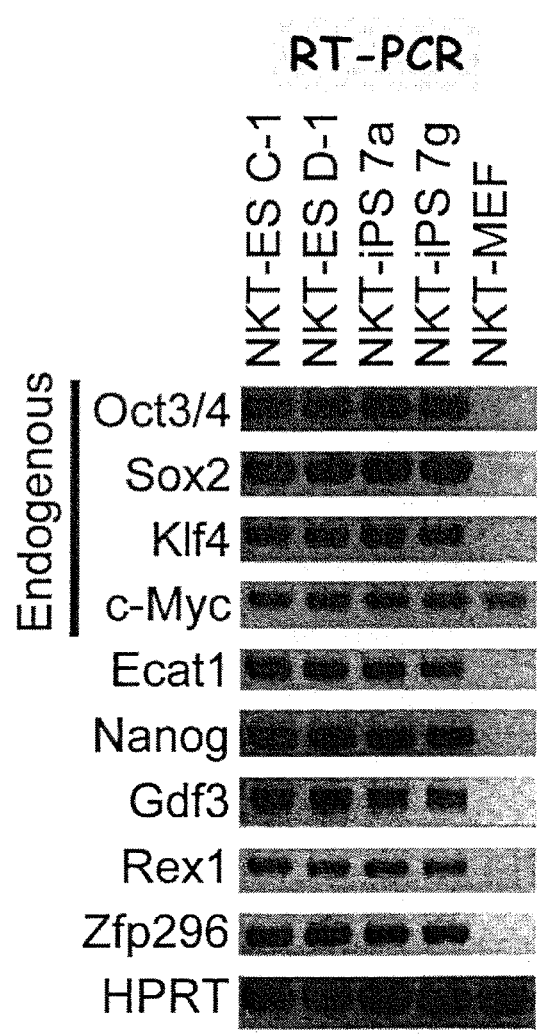
FIG. 18 is a drawing showing a gene expression analysis of NKT-iPS cell clones 7a and 7g.
Figure 19:
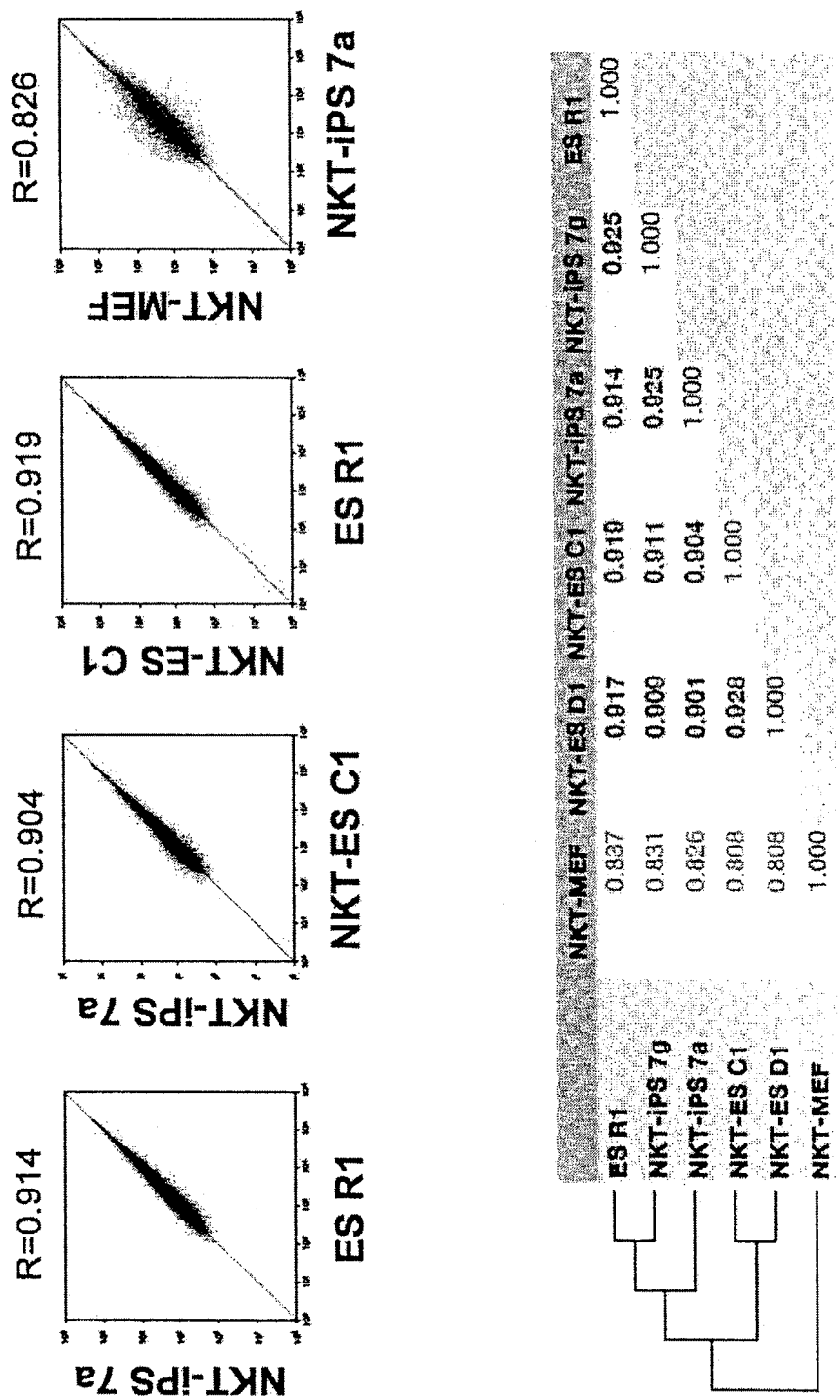
FIG. 19 is a drawing showing a DNA microarray analysis and correlation analysis of NKT-iPS cell clones 7a and 7g.
Figure 20:
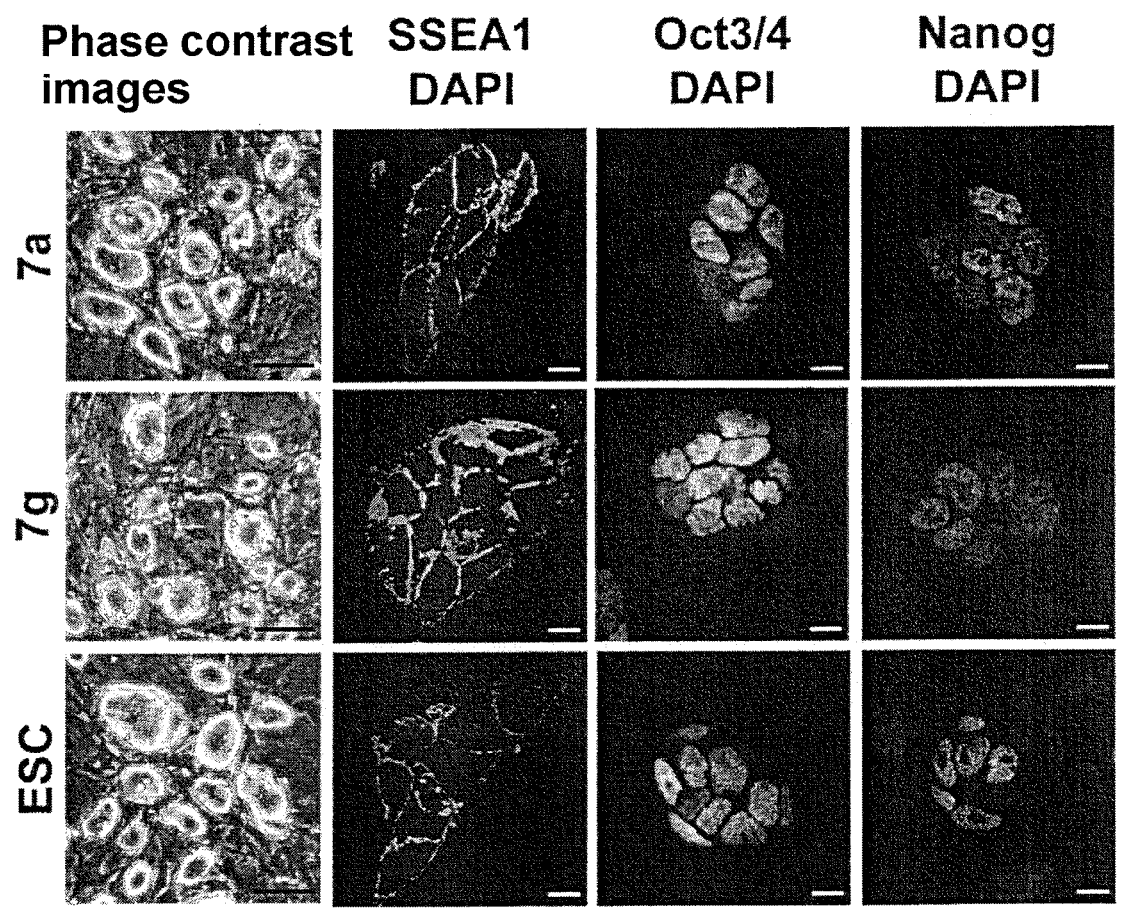
FIG. 20 is a drawing showing morphological examination of NKT-iPS cell clones 7a and 7g and the expression of ES cell markers.
Figure 21:
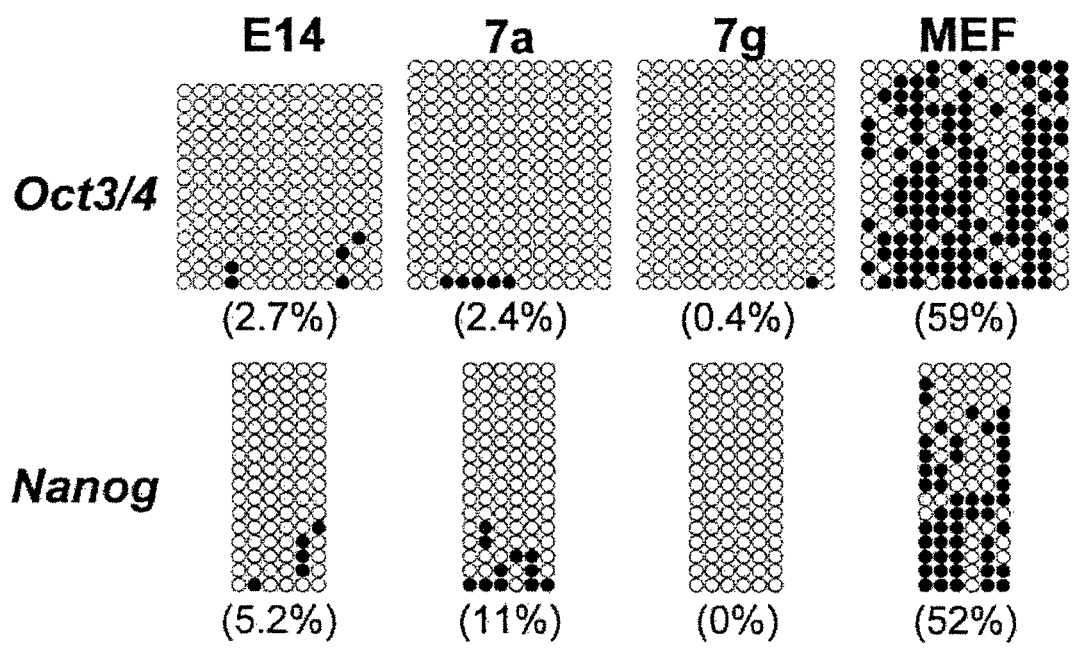
FIG. 21 is a drawing showing a DNA methylation analysis of NKT-iPS cell clones 7a and 7g.
Figure 22:
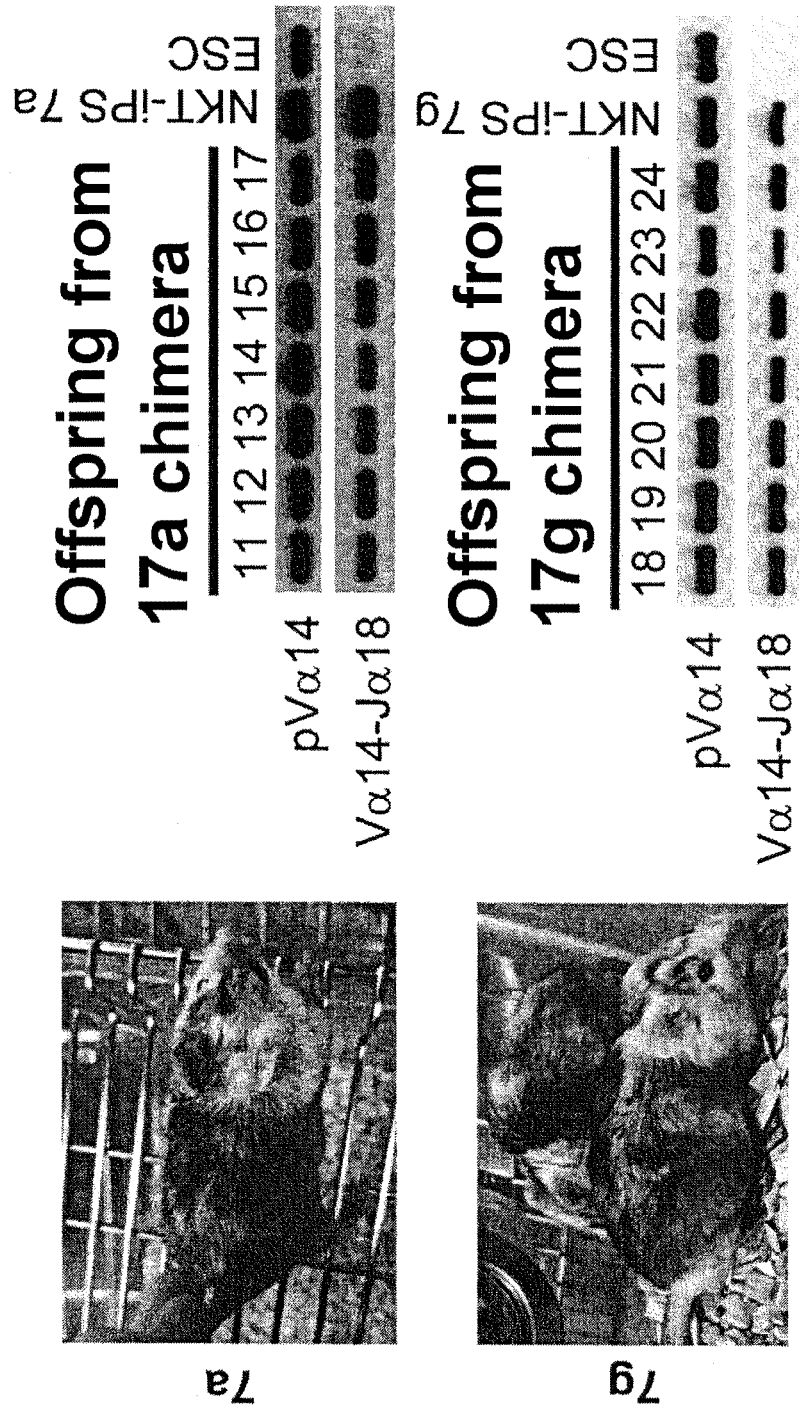
FIG. 22 is a drawing showing the transmission of NKT-iPS cell clones 7a and 7g to offspring.

Establishment of iPS Cells Derived from NKT Clone Mouse-Derived Embryonic Fibroblasts The conventional method of establishing a mouse iPS cell, established by Yamanaka et al., is based on the introduction of Oct3/4, Sox2, Klf4, and c-Myc into an embryonic fibroblast (MEF). Hence, an attempt was made to establish an iPS cell from MEF of an NKT clone mouse created in Generation Example 1, and NKT-iPS cells 7a and 7g were successfully established. The established 7a and 7g were confirmed as having the T cell receptor region undergoing gene rearrangement to the T cell receptor of NKT cells (FIG. 17), and were also confirmed by a RT-PCR method as being equivalent to ES cells in terms of the expression of a group of genes that can be ES cell markers (FIG. 18). Also, a comprehensive gene expression analysis using a DNA microarray and a cluster analysis thereof yielded results showing that the established 7a and 7g were close to ES cells and distant from the starting MEF of the NKT clone mouse (FIG. 19). Furthermore, morphological examination thereof was performed; it was also confirmed that 7a and 7g were morphologically very similar to ES cells, and that the ES cell markers SSEA1, Oct3/4, and Nanog were expressed (FIG. 20). Furthermore, the genome methylation tendency of the gene expression regulatory regions of Oct3/4 and Nanog was analyzed, demonstrating sufficient reprogramming in 7a and 7g, wherein the genomes were unmethylated to the same extent as with the ES cells (FIG. 21). Also, a plurality of chimeric mice were born from 7a and 7g, and all the offspring obtained by crossing with a C57BL/6 mouse exhibited gene rearrangement to the T cell receptor of NKT cells, confirming transmission to offspring, and demonstrating that 7a and 7g possess pluripotency (FIG. 22). From the above, it was concluded that 7a and 7g satisfied the criteria for iPS cells.

Example 12

In Vitro Differentiation Induction from the iPS Cell of Example 11 to NKT Cells

Figure 23:
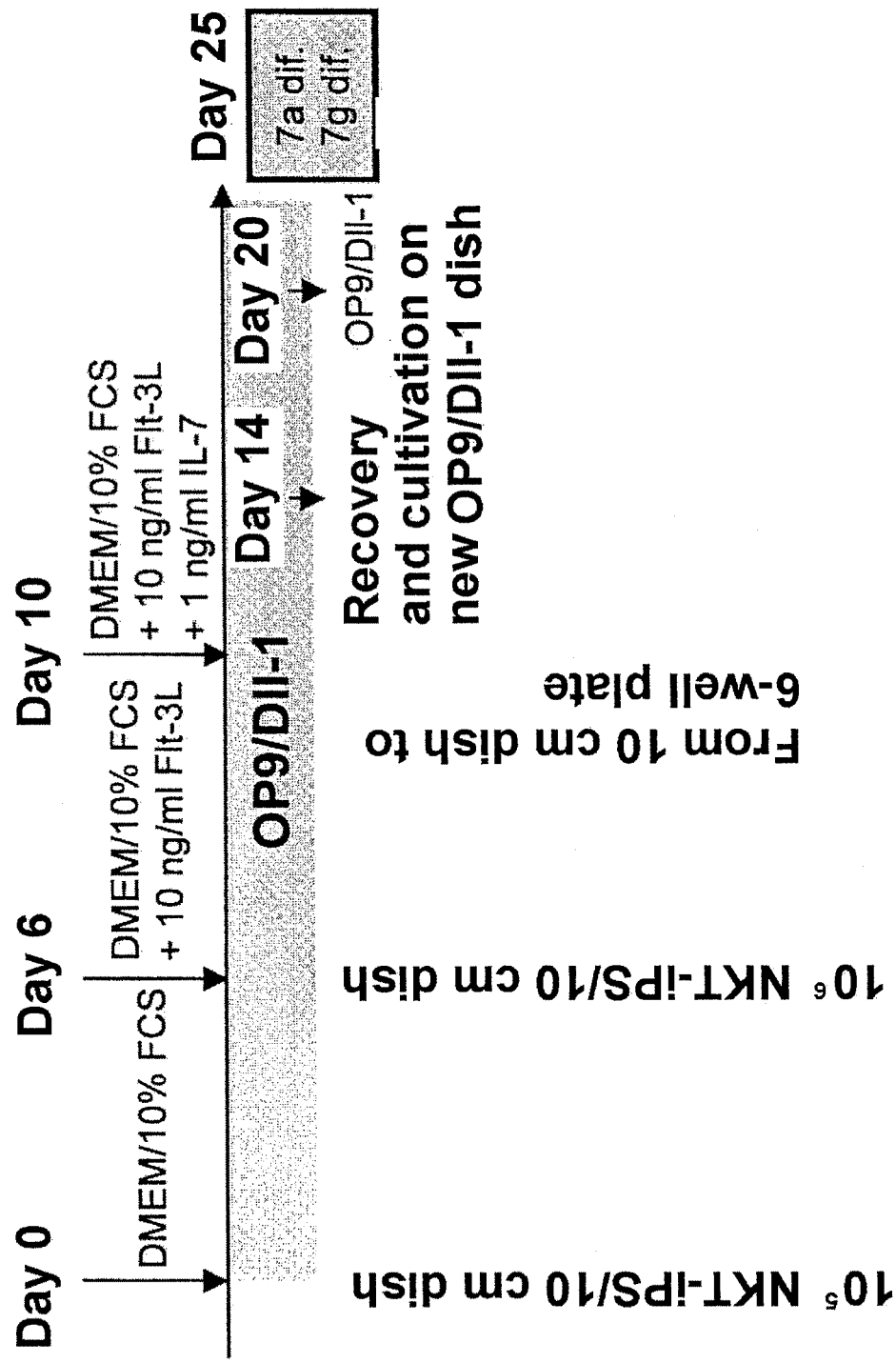
FIG. 23 is a drawing showing a method of in vitro induction of differentiation of NKT cells from NKT-iPS cell clones 7a and 7g.
Figure 25:
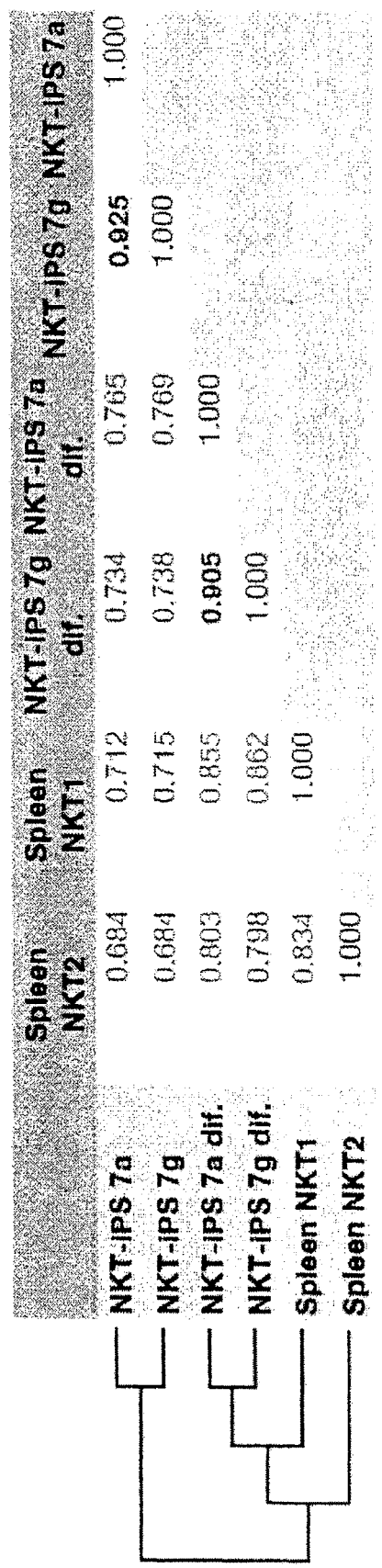
FIG. 25 is a drawing showing a comprehensive gene expression correlation analysis of cells 7a dif. and 7g dif. differentiation-induced in vitro.
Figure 26:
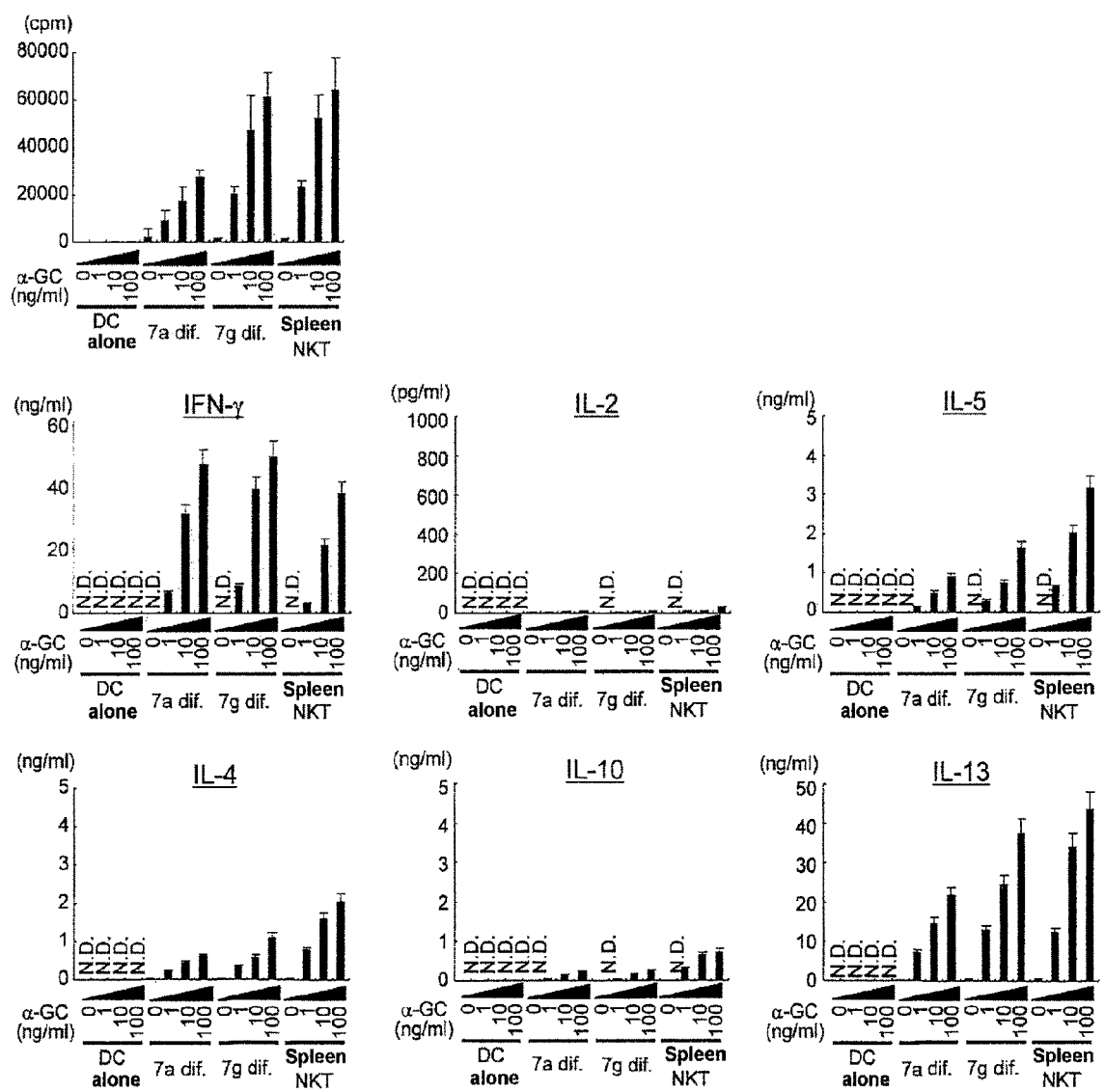
FIG. 26 is a drawing showing an in vitro functional analysis of cells 7a dif. and 7g dif. differentiation-induced in vitro.

Next, an investigation was performed to determine whether it was possible to differentiation-induce NKT cells from MEF-derived 7a and 7g in vitro. 7a and 7g were co-cultured with OP9/Dll-1, a cell line prepared by forcing the bone marrow-derived stromal cell OP9 to express the Notch ligand Dll-1, per the protocol shown in FIG. 23 for 25 days. As a result, as shown in FIG. 24, it was demonstrated that 7a and 7g were differentiation-induced to α-GalCer/CD1d dimer-positive TCRβ-positive NKT cell-like cells (7a dif. and 7g dif.). Furthermore, 7a dif. and 7g dif. were very similar to what are called DP cells, which are CD4-positive CD8-positive cells present in the thymus, in terms of the expression of cell surface markers. Also, a comprehensive gene expression analysis using a DNA microarray and a cluster analysis thereof yielded results showing that 7a dif. and 7g dif. are distant from the 7a and 7g before differentiation induction and close to spleen-derived NKT cells present in the periphery (FIG. 25). Hence, to determine whether 7a dif. and 7g dif. are functionally equivalent to NKT cells, they were stimulated with the glycolipid ligand α-GalCer while being co-cultured with dendritic cells, and examined for a proliferation potential and cytokine productivity. As a result, it was confirmed that 7a dif. and 7g dif., like peripheral NKT cells, possess a remarkable proliferation potential and the capability of producing large amounts of IFN-γ and IL-4 (FIG. 26).

Example 13

In Vivo Functional Analysis of 7a Dif. and 7g Dif.

Figure 27:
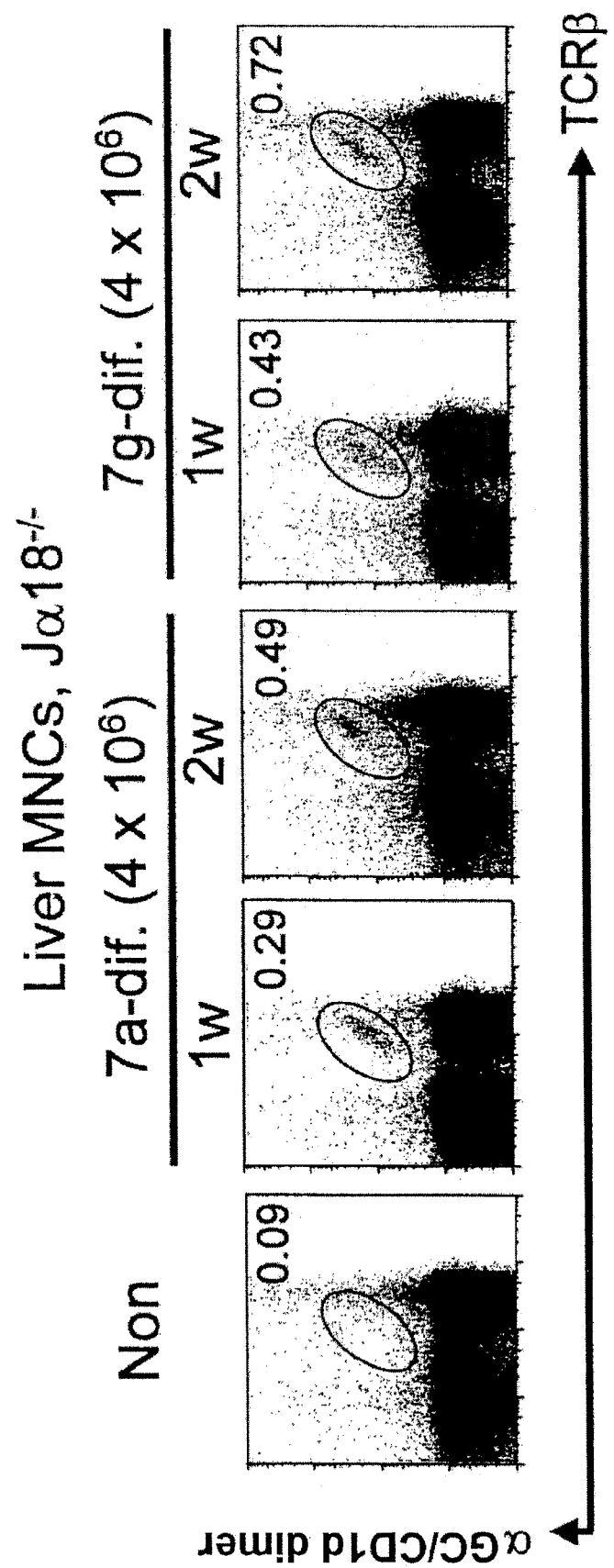
FIG. 27 is a drawing confirming the presence of transferred genes at 1 week (1 w) and 2 week (2 w) after transfer of cells 7a dif. and 7g dif. differentiation-induced in vitro into an NKT cell-deficient mouse.
Figure 28:
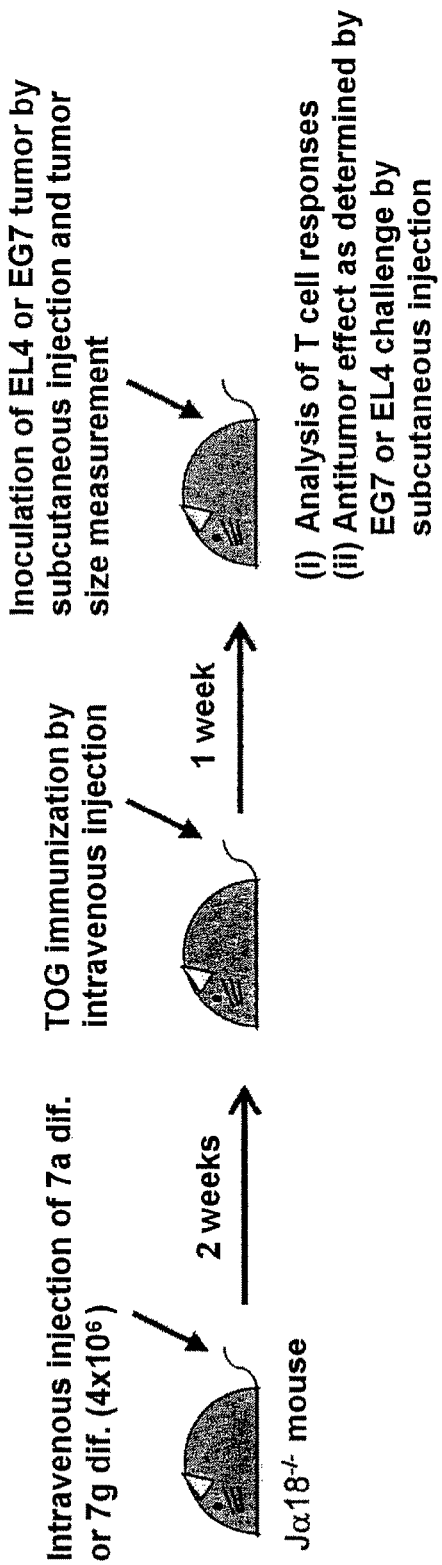
FIG. 28 is a drawing showing the protocol of an in vivo evaluation of cells 7a dif. and 7g dif. differentiation-induced in vitro.
Figure 30:
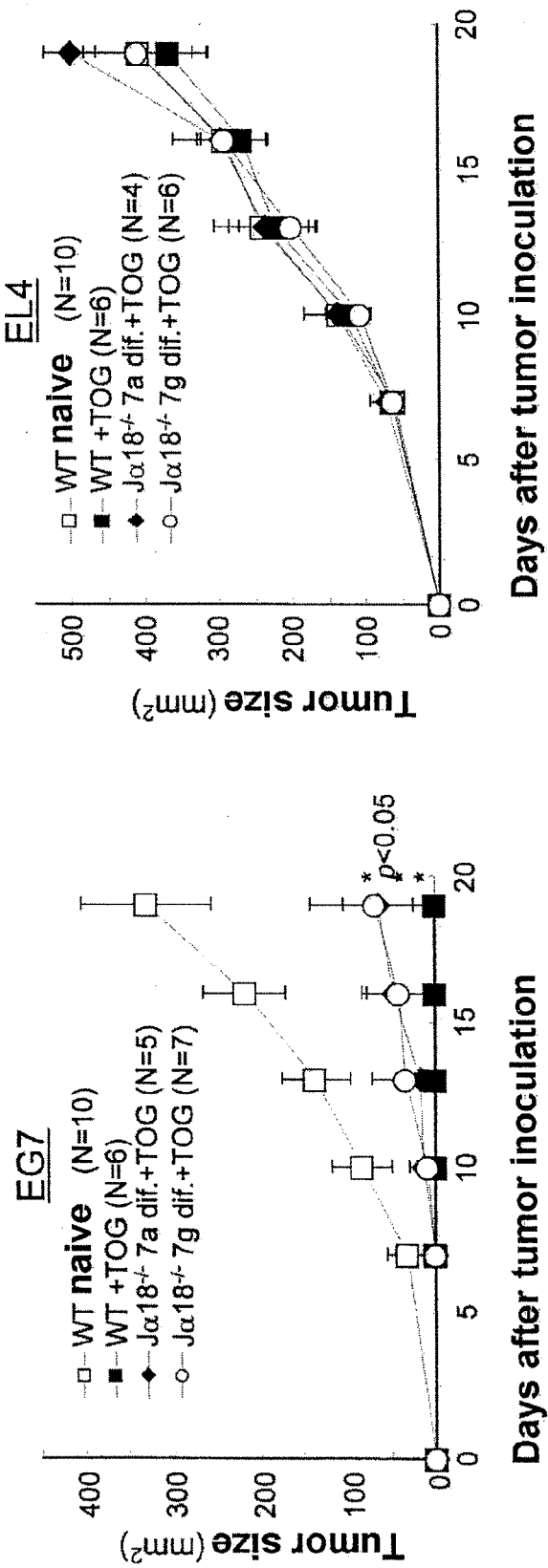
FIG. 30 is a drawing showing the malignant tumor rejection by cells 7a dif. and 7g dif. differentiation-induced in vitro.

Since 7a dif. and 7g dif. are functionally equivalent to peripheral NKT cells, as described in Example 12, an analysis was performed to determine whether the same effect is present in vivo using an NKT cell-deficient mouse. After 7a dif. and 7g dif. were transferred to the NKT cell-deficient mouse, the presence of the transferred cells at 1 week and 2 weeks was checked; it was demonstrated that α-GalCer/CD1d dimer-positive, TCRβ-positive 7a dif. and 7g dif. were present in the liver (FIG. 27). Hence, on the basis of the protocol shown in FIG. 28, the induction of antigen specific CD8-positive T cells and an accompanying antitumor effect were checked. TAP knockout mouse-derived splenocytes were cultured with 10 mg/ml ovalbumin (OVA) in a hypertonic solution, after which apoptosis was induced, and $2 \times 10^7$ apoptotic cells, along with 2 μg of α-GalCer, were transferred to the NKT cell-deficient mouse having 7a dif. and 7g dif. transferred thereto one week previously (TOG immunization). Seven days later, splenocytes were collected from the mouse, stimulated with OVA peptide (257-264) in vitro, and analyzed for IFN-γ production by intracellular staining. As a result, it was confirmed that OVA-antigen specific CD8-positive T cells possessing IFN-γ productivity had been induced equivalently to a wild type mouse, demonstrating that 7a dif. and 7g dif. function in vivo and have a potent adjuvant effect (FIG. 29). Hence, the mouse was evaluated using a malignant tumor rejection model using the C57BL/6 mouse thymoma cell line EL4 or EG7 (EL4 OVA-transfectant). As a result, with EG7, which is a cell line that forcibly expresses OVA, the non-TOG-immunized wild type mouse exhibited a progression of the malignant tumor, whereas in the TOG-immunized 7a dif.- and 7g dif.-transferred NKT cell-deficient mouse, no progression was found as in the TOG-immunized wild type mouse. With EL4, similar progression was observed in the TOG-immunized wild type mouse and the NKT cell-deficient mouse; therefore, it was concluded that the progression was attributed to the antigen-specific adjuvant effect of the transferred 7a dif. and 7g dif. (FIG. 30).

The results above show that any cells having a T cell receptor rearranged therein can be differentiation-induced into functional immunocompetent cells rearranged to the T cell receptor.

Example 14

How to Establish iPS Cells from Wild Type NKT Cells Efficiently

While the present inventors succeeded in establishing iPS cells from an NKT cell derived from a splenocyte of a wild type mouse, as shown in Example 10, a more efficient method of establishing iPS cells was secured.

Figure 31:
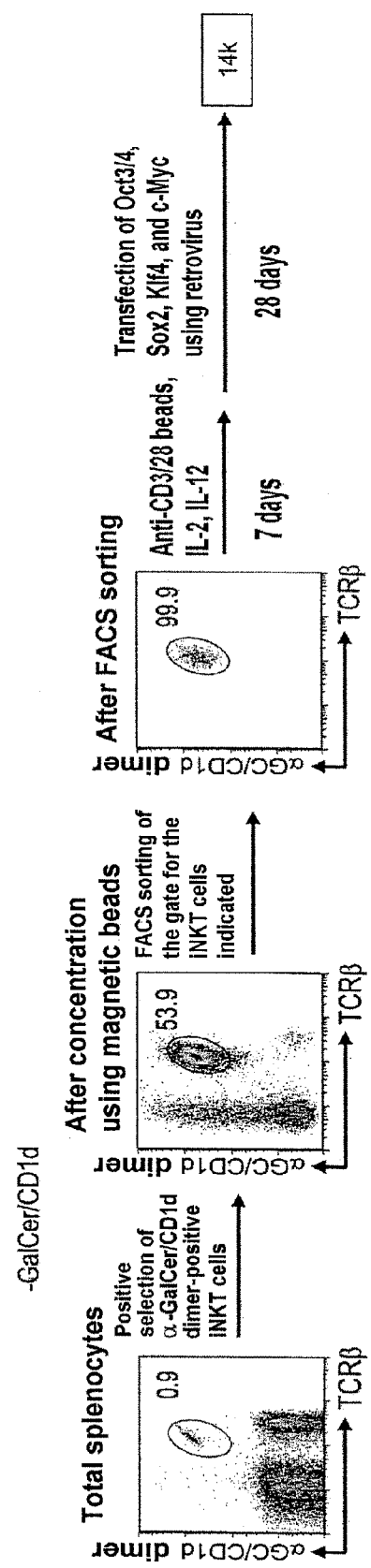
FIG. 31 is a drawing showing a method of efficiently establishing an iPS cell from a wild type NKT cell.
Figure 32:
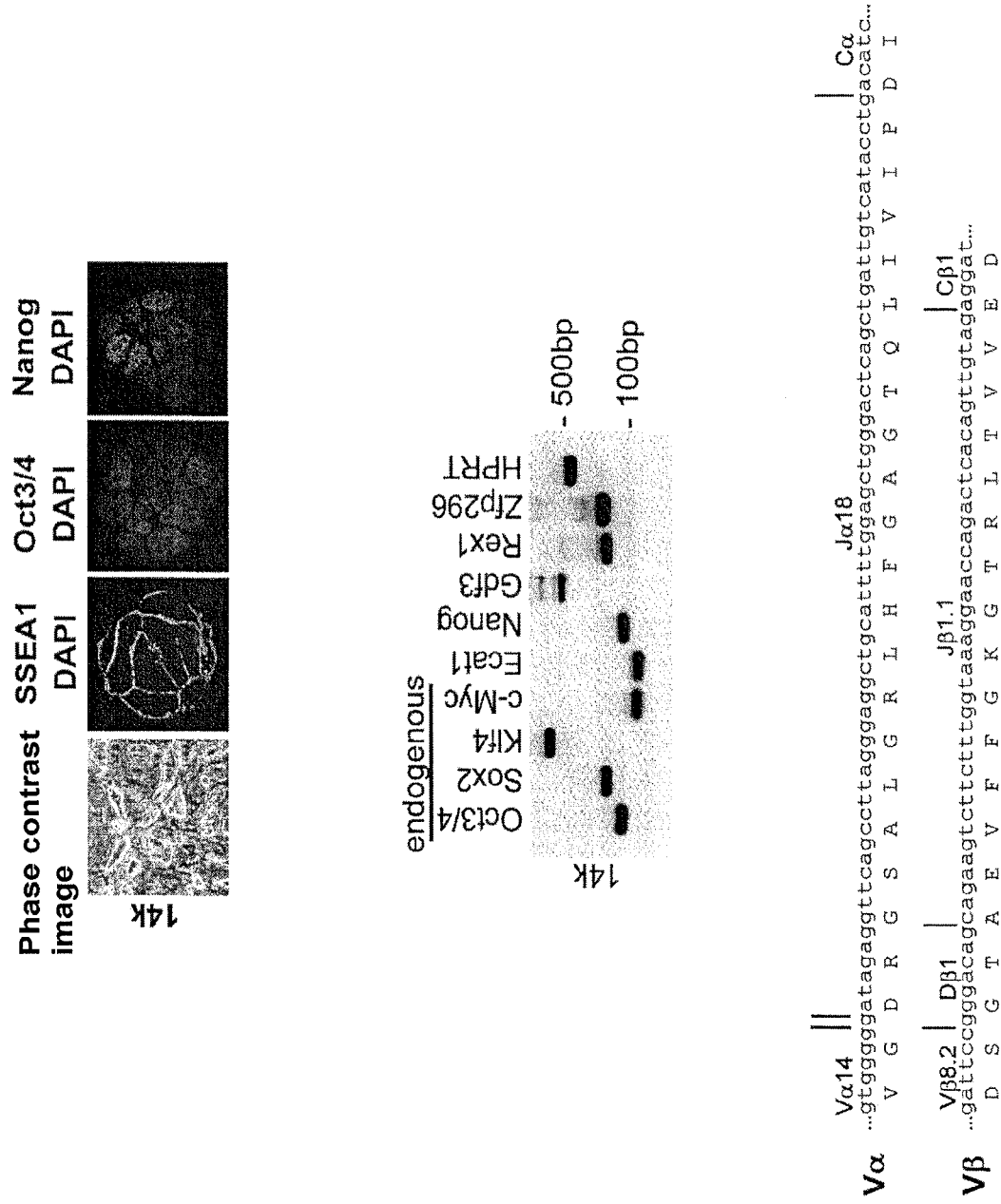
FIG. 32 is a drawing showing properties of NKT-iPS clone 14k.

That is, CD1d-restricted NKT cells are concentrated from splenocytes using MACS beads, after which NKT cells of 99.9% purity are obtained by FACS sorting. The NKT cells can be forced to enter a proliferation cycle by adding IL-2 (10 ng/ml) and IL-12 (10 ng/ml) under stimulation with an anti- CD3 antibody (10 µg/ml) and an anti-CD28 antibody (10 µg/ml). It became evident that by infecting the NKT cells with a retrovirus harboring nucleic acids that encode Oct3/4, Sox2, Klf4, and c-Myc under these conditions, iPS cells could be established more than 10 times more efficiently than in Example 10, whereby the inventors succeeded in establishing NKT-iPS clone 14k (FIG. 31). As shown in FIG. 32, 14k exhibits an ES cell-like morphology, the expression of ES cell markers, and rearrangement of the NKT cell T cell receptor in the T cell receptor region. Also, as examined by the method described in Example 12, differentiation into NKT cell-like cells was seen, which proliferated with glycolipid stimulation in vitro and became cytokine-producing functional cells (FIG. 33).

INDUSTRIAL APPLICABILITY

According to the present invention, it is possible to redifferentiate NKT cells via iPS cells that are likely undergo differentiation induction to NKT-like cells, that is, NKT-iPS cells, and to expand the NKT cells in large amounts or differentiation-induce the same to mature NKT cells in vitro; therefore, an NKT cell cytotherapy agent can be provided in large amounts conveniently and at low cost, and is extremely useful in cancer immunotherapy, infection defense, and treatment of allergic diseases and the like.

This application is based on a patent application No. 2008-230292 filed in Japan (filing date: Sep. 8, 2008), the contents of which are incorporated in full herein.

The invention claimed is:

1. A method of generating a mature NKT cell, comprising
(a) providing a CD4/CD8-double positive NKT cell, wherein the CD4/CD8-double positive NKT cell was obtained by co-culturing a cloned cell with a stromal cell that expresses a Notch ligand as a feeder cell in the presence of interleukin-7 and Flt3 ligand, and wherein the cloned cell has been obtained by
  (i) transducing a somatic cell having the α-chain region of the T cell antigen receptor gene rearranged to uniform Vα-Jα in an NKT cell receptor-specific way with retroviral vectors comprising nucleic acid sequences encoding nuclear reprogramming factors, wherein the nuclear reprogramming factors comprise Oct3/4, Sox2, Klf4, and one or more of c-Myc, Nanog, and Lin28, wherein Sox2 is replaceable with Sox1, Sox3, Sox15, Sox17, or Sox18, Klf4 is replaceable with Klf1, Klf2, or Klf5, and c-Myc is replaceable with T58A (active mutant), N-Myc, or L-Myc, and
  (ii) culturing the somatic cell obtained in step (i) under conditions suitable for the cultivation of embryonic stem (ES) cells while maintaining the pluripotency of the ES cells, to produce a cloned cell, wherein the cloned cell has (A) the α-chain region of the T cell antigen receptor gene rearranged to uniform Vα-Jα in an NKT cell receptor-specific way, and (B) pluripotency and replication competence, and
(b) co-culturing the CD4/CD8-double positive NKT cell of step (a) with a stromal cell that does not express a Notch ligand as a feeder cell in the presence of three or more cytokines selected from the group consisting of interleukin-2, interleukin-7, interleukin-15 and Flt3 ligand to produce a mature NKT cell.

2. The method according to claim 1, wherein the cultivation in step (b) is performed in the presence of interleukin-15.

3. The method according to claim 1, wherein the somatic cell is an NKT cell.

4. The method according to claim 1, wherein the somatic cell is a fibroblast.

5. The method according to claim 1, wherein the somatic cell is of human derivation.

6. The method according to claim 1, wherein the method further comprises co-culturing the cloned cell with a stromal cell that expresses a Notch ligand as a feeder cell in the presence of interleukin-7 and Flt3 ligand to provide the CD4/CD8-double positive NKT cell.

7. The method according to claim 6, wherein the method further comprises
(i) transducing a somatic cell having the α-chain region of the T cell antigen receptor gene rearranged to uniform Vα-Jα in an NKT cell receptor-specific way with retroviral vectors comprising nucleic acid sequences encoding nuclear reprogramming factors, wherein the nuclear reprogramming factors comprise Oct3/4, Sox2, Klf4, and one or more of c-Myc, Nanog, and Lin28, wherein Sox2 is replaceable with Sox1, Sox3, Sox15, Sox17, or Sox18, Klf4 is replaceable with Klf1, Klf2, or Klf5, and c-Myc is replaceable with T58A (active mutant), N-Myc, or L-Myc, and
(ii) culturing the somatic cell obtained in step (i) under conditions suitable for the cultivation of embryonic stem (ES) cells while maintaining the pluripotency of the ES cells, to produce a cloned cell, wherein the cloned cell has (A) the α-chain region of the T cell antigen receptor gene rearranged to uniform Vα-Jα in an NKT cell receptor-specific way, and (B) pluripotency and replication competence.

8. The method according to claim 7, wherein the somatic cell is an NKT cell, and the NKT cell contacted with the nuclear reprogramming factors has been stimulated with an anti-CD3 antibody and an anti-CD28 antibody in the presence of interleukin-2 and interleukin-12.

9. The method according to claim 7, wherein the nuclear reprogramming factors are Oct3/4, Sox2, Klf4 and c-Myc.

10. The method of claim 7, wherein the somatic cell obtained in step (i) is cultured on mouse embryonic feeder cells in step (ii) to produce the cloned cell.

11. The method of claim 10, wherein the conditions of step (ii) include the presence of basic fibroblast growth factor (bFGF) or leukemia inhibitory factor (LIF).

12. The method according to claim 7, wherein the cultivation in step (b) is performed in the presence of interleukin-15.

13. The method according to claim 7, wherein the somatic cell is an NKT cell.

14. The method according to claim 7, wherein the somatic cell is a fibroblast.

15. The method according to claim 7, wherein the somatic cell is of human derivation.

16. The method according to claim 1, wherein the mature NKT cell is an NK1.1 positive NKT cell.

17. The method according to claim 1, wherein the mature NKT cell is a CD3ε positive NKT cell.

* * * * *

```
SEQUENCE LISTING

<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
gacccaagtg gagcagagtc ct                                              22

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tcacctatgt ctcctggaag cctc                                            24

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
cagctccaaa atgcagcctc cctaa                                           25

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tctttccacc aggcccccgg ctc                                             23

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
tgcgggcgga catggggaga tcc                                             23
```

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
tagagctaga ctccgggcga tga                                              23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
ttgccttaaa caagaccacg aaa                                              23

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
gcgaactcac acaggcgaga aacc                                             24

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
tcgcttcctc ttcctccgac aca                                              23

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
tgacctaact cgaggaggag ctggaatc                                         28

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
aagtttgagg cagttaaaat tatggctgaa gc                                    32

<210> SEQ ID NO 12
<211> LENGTH: 28
<212> TYPE: DNA
<213> ORGANISM: Artificial Sequence
<220> FEATURE:

```
<223> OTHER INFORMATION: Primer

<400> SEQUENCE: 12
tgtggggccc tgaaaggcga gctgagat                                          28

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
atgggccgcc atacgacgac gctcaact                                          28

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caggtgtttg agggtagctc                                                   20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cggttcatca tggtacagtc                                                   20

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gttccaacct gtgcctcgcg tctt                                              24

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
agcgaggcat ggagagagcg gagcag                                            26

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
acgagtggca gtttcttctt ggga                                              24
```

```
<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
tatgactcac ttccaggggg cact                                          24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
ccattagggg ccatcatcgc tttc                                          24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
cactgctcac tggagggggc ttgc                                          24

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ctgtgtgctc aaggggggct                                               20

<210> SEQ ID NO 23
<211> LENGTH: 29
<212> TYPE: DNA
<213> ORGANISM: Artificial Sequence
<220> FEATURE:
<223> OTHER INFORMATION: Primer

<400> SEQUENCE: 23
ggactcctcg tatttgcaga ttcaacttg                                     29
```